US012774461B2

(12) United States Patent
Oren et al.

(10) Patent No.: US 12,774,461 B2
(45) Date of Patent: Oct. 27, 2026

(54) EXPRESSED BARCODE LIBRARIES AND USES THEREOF

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Yaara Oren, Cambridge, MA (US); Aviv Regev, Cambridge, MA (US); Joan Brugge, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 51 days.

(21) Appl. No.: 16/563,450

(22) Filed: Sep. 6, 2019

(65) Prior Publication Data

US 2020/0080076 A1 Mar. 12, 2020

Related U.S. Application Data

(60) Provisional application No. 62/728,701, filed on Sep. 7, 2018.

(51) Int. Cl.
*C12N 15/10* (2006.01)
*C40B 20/04* (2006.01)
(Continued)

(52) U.S. Cl.
CPC ..... *C12N 15/1065* (2013.01); *C12N 15/1086* (2013.01); *C40B 20/04* (2013.01);
(Continued)

(58) Field of Classification Search
CPC ............ C12N 15/1065; C12N 15/1086; C12N 2810/60; C12N 2830/008; C12N 2830/34;
(Continued)

(56) References Cited

U.S. PATENT DOCUMENTS 4,405,712 A 9/1983 Vande et al.
4,650,764 A 3/1987 Temin et al.
(Continued)

FOREIGN PATENT DOCUMENTS

WO 89/05345 A1 6/1989
WO 90/06997 A1 6/1990
(Continued)

OTHER PUBLICATIONS

Guernet et al. "CRISPR-Barcoding for Intratumor Genetic Heterogeneity Modeling and Functional Analysis of Oncogenic Driver Mutations" Molecular Cell 63, 526-538, Aug. 4, 2016 (Year: 2016).*

(Continued)

*Primary Examiner* — Aaron A Priest
*Assistant Examiner* — Randi Lynn Beil
(74) *Attorney, Agent, or Firm* — GTC Law Group PC & Affiliates

(57) ABSTRACT

Disclosed herein are nucleic acid molecules comprising molecular barcodes having a variable sequence operably linked to a promoter and compositions comprising such nucleic acid molecules. Further disclosed herein are methods for simultaneously mapping the lineage and the transcriptional state of a cell.

37 Claims, 29 Drawing Sheets

Specification includes a Sequence Listing.

(51) Int. Cl.
*C40B 40/06* (2006.01)
*C40B 70/00* (2006.01)

(52) U.S. Cl.
CPC .............. *C40B 40/06* (2013.01); *C40B 70/00* (2013.01); *C12N 2810/60* (2013.01); *C12N 2830/008* (2013.01); *C12N 2830/34* (2013.01); *C12N 2840/206* (2013.01)

(58) Field of Classification Search
CPC ... C12N 2840/206; C40B 20/04; C40B 40/06; C40B 70/00
USPC .............................................................. 506/4
See application file for complete search history.

(56) References Cited

U.S. PATENT DOCUMENTS

| | | | |
|---|---|---|---|
| 5,252,479 A | 10/1993 | Srivastava | |
| 6,277,633 B1 | 8/2001 | Olsen | |
| 6,312,682 B1 | 11/2001 | Kingsman et al. | |
| 6,312,683 B1 | 11/2001 | Kingsman et al. | |
| 6,521,457 B2 | 2/2003 | Olsen | |
| 6,669,936 B2 | 12/2003 | Kingsman et al. | |
| 6,808,923 B2 | 10/2004 | Engelman et al. | |
| 6,897,024 B2 | 5/2005 | Bussemakers et al. | |
| 6,924,123 B2 | 8/2005 | Kingsman et al. | |
| 7,056,699 B2 | 6/2006 | Kingsman et al. | |
| 7,198,784 B2 | 4/2007 | Kingsman et al. | |
| 7,247,297 B2 | 7/2007 | Weichselbaum et al. | |
| 7,321,030 B2 | 1/2008 | Hamada et al. | |
| 7,364,727 B2 | 4/2008 | Li et al. | |
| 7,816,131 B2 | 10/2010 | Hung et al. | |
| 8,034,914 B2 | 10/2011 | Hochberg | |
| 2008/0213220 A1 | 9/2008 | Fisher et al. | |
| 2009/0311664 A1 | 12/2009 | Fong et al. | |
| 2010/0111128 A1 | 5/2010 | Qin et al. | |
| 2020/0017883 A1* | 1/2020 | Schiller et al. | C12N 15/907 |

FOREIGN PATENT DOCUMENTS

| | | |
|---|---|---|
| WO | 92/05266 A2 | 4/1992 |
| WO | 92/07573 A1 | 5/1992 |
| WO | 92/14829 A1 | 9/1992 |

OTHER PUBLICATIONS

Guernet et al. "CRISPR-Barcoding for Intratumor Genetic Heterogeneity Modeling and Functional Analysis of Oncogenic Driver Mutations" Molecular Cell 63 Suppl Information, 19 pages with Figures S1-S7, Tables S1-S3, Suppl Exp Proc, and Suppl Refs, Aug. 4, 2016 (Year: 2016).*

Tsui "Genetic markers on chromosome 7" Journal of Medical Genetics 1988, 25, 294-306 (Year: 1988).*

Hohensinner et al. "PAI-1 (Plasminogen Activator Inhibitor-1) Expression Renders Alternatively Activated Human Macrophages Proteolytically Quiescent" Arterioscler Thromb Vasc Biol. 2017, 37:1913-1922; DOI: 10.1161/ATVBAHA.117.309383 (Year: 2017).*

Zhang et al. "Plasminogen activator inhibitor-1 promotes the proliferation and inhibits the apoptosis of pulmonary fibroblasts by Ca2+ signaling" Thrombosis Res. 2013, 131:64-71 (Year: 2013).*

Webb et al. "An internal ribosome entry site in the 5' untranslated region of epidermal growth factor receptor allows hypoxic expression" Oncogenesis (2015) 4, e134; doi:10.1038/oncsis.2014.43 (Year: 2015).*

Oshimura et al. ("A pathway from chromosome transfer to engineering resulting in human and mouse artificial chromosomes for a variety of applications to bio-medical challenges" Chromosome Res (2015) 23:111-133; DOI 10.1007/s10577-014-9459-z (Year: 2015).*

Nguyen et al. "Clonal Analysis via Barcoding Reveals Diverse Growth and Differentiation of Transplanted Mouse and Human Mammary Stem Cells" Cell Stem Cell 14, 253-263, Feb. 6, 2014 (Year: 2014).*

Cheung et al. "Analysis of the clonal growth and differentiation dynamics of primitive barcoded human cord blood cells in NSG mice" BLOOD, Oct. 31, 2013, vol. 122:18, 3129-3137 (Year: 2013).*

Le Devedec et al. "Two-Photon Intravital Multicolor Imaging Combined with Inducible Gene Expression to Distinguish Metastatic Behavior of Breast Cancer Cells In Vivo" Mol Imaging Biol (2011) 13:67-77 (Year: 2011).*

Map of pRSI9-U6-(sh)-UbiC-TagRFP-2A-Puro (four sheets download from https://www.addgene.org/28289/ (Year: 2015).*

Ramirez et al. "Diverse drug-resistance mechanisms can emerge from drug-tolerant cancer persister cells" Nat Commun. 2016; 7:10690, Published online Feb. 19, 2016, doi: 10.1038/ncomms10690 (Year: 2016).*

Alexeyev et al. "A retro-lentiviral system for doxycycline-inducible gene expression and gene knockdown in cells with limited proliferative capacity" Mol Biol Rep (2010) 37:1987-1991 DOI 10.1007/s11033-009-9647-7 (Year: 2010).*

Schröder et al. "A single-stranded promoter for RNA polymerase III" Proc Nat'l Acad Sci, Feb. 2003, 100 (3):934-939; DOI: 10.1073/pnas.242735699 (Year: 2003).*

Shearwin et al. "Transcriptional interference—a crash course" Trends Genet. 2005; 21(6):339-345; doi:10.1016/j.tig.2005.04.009 (Year: 2005).*

Cox et al. A synthetic three-color scaffold for monitoring genetic regulation and noise. Journal of Biological Engineering. 4, 2010, p. 1-12 [online], [retrieved on Feb. 22, 2024]. Retrieved from the Internet: <URL:https://link.springer.com/article/10.1186/1754-1611-4-10><DOI:10.1186/1754-1611-4-10> (Year: 2010).*

Aguirre-Ghiso, "Models, Mechanisms and Clinical Evidence for Cancer Dormancy", Nature Reviews Cancer, vol. 7, No. 11, Nov. 2007, 31 pages.

Zabner, et al., "Safety and Efficacy of Repetitive Adenovirus-Mediated Transfer of CFTR CDNA to Airway Epithelia of Primates and Cotton Rats", Nature Genetics, vol. 6, No. 1, Jan. 1994, 75-83.

Bhang, et al., "Studying Clonal Dynamics in Response to Cancer Therapy using High-Complexity Barcoding", Nature Medicine, vol. 21, No. 5, May 2015, 440-448.

Blaese, et al., "T Lymphocyte-Directed Gene Therapy for ADA-SCID: Initial Trial Results after 4 Years", Science, vol. 270, No. 5235, Oct. 20, 1995, 475-480.

Boshart, et al., "A Very Strong Enhancer Is Located Upstream of an Immediate Early Gene of Human Cytomegalovirus", Cell, vol. 41, No. 2, Jun. 1985, 521-530.

Bowtell, et al., "Rethinking Ovarian Cancer II: Reducing Mortality from High-Grade Serous Ovarian Cancer", Nature Reviews Cancer, vol. 15, No. 11, Nov. 2015, 31 pages.

Brown, "TGF-β-Induced Quiescence Mediates Chemoresistance of Tumor-Propagating Cells in Squamous Cell Carcinoma", Cell Stem Cell, vol. 21, No. 5, Nov. 2, 2017, 35 pages.

Chien, et al., "Platinum-Sensitive Recurrence in Ovarian Cancer: The Role of Tumor Microenvironment", Frontiers in Oncology, vol. 3, Article 251, Sep. 24, 2013, 6 pages.

Cotten, et al., "High-Efficiency Receptor-Mediated Delivery of Small and Large (48 Kilobase Gene Constructs Using the Endosome-Disruption Activity of Defective or Chemically Inactivated Adenovirus Particles", Proceedings of the National Academy of Sciences of the United States of America, vol. 89, No. 13, Jul. 1, 1992, 6094-6098.

Cunnea, et al., "Modeling Platinum Sensitive and Resistant High-Grade Serous Ovarian Cancer: Development and Applications of Experimental Systems", Frontiers in Oncology, vol. 4, Article 81, Apr. 2014, 8 pages.

Danos, et al., "Safe and Efficient Generation of Recombinant Retroviruses with Amphotropic and Ecotropic Host Ranges", Proceedings of the National Academy of Sciences of the United States of America, vol. 85, No. 17, Sep. 1988, 6460-6464.

Donahue, et al., "Reduction In SIV Replication in Rhesus Macaques Infused with Autologous Lymphocytes Engineered with Antiviral Genes", Nature Medicine, vol. 4, Feb. 1, 1998, 181-186.

Doronin, et al., "Tissue-Specific, Tumor-Selective, Replication-Competent Adenovirus Vector for Cancer Gene Therapy", Journal of Virology, vol. 75, No. 7, Apr. 2001, 3314-3324.

(56) References Cited

OTHER PUBLICATIONS

Geller, et al., "A Defective HSV-1 Vector Expresses Escherichia Coli Beta-Galactosidase in Cultured Peripheral Neurons", Science, vol. 241, No. 4873, Sep. 23, 1988, 1667-1669.
Goldman, et al., "Lentiviral Vectors for Gene Therapy of Cystic Fibrosis", Human Gene Therapy, vol. 8, No. 18, Dec 10, 1997, 2261-2268.
Graham, et al., "Manipulation of Adenovirus Vectors", Methods in Molecular Biology, vol. 7, 1991, 109-128.
Greelish, et al., "Stable Restoration of the Sarcoglycan Complex in Dystrophic Muscle Perfused with Histamine and a Recombinant Adeno-Associated Viral Vector", Nature Medicine, vol. 5, No. 4, Apr. 1999, 439-443.
Hallenbeck, et al., "A Novel Tumor-Specific Replication-Restricted Adenoviral Vector for Gene Therapy of Hepatocellular Carcinoma", Human Gene Therapy, vol. 10, No. 10, Jul. 1, 1999, 1721-1733.
Herzog, et al., "Long-Term Correction of Canine Hemophilia B by Gene Transfer of Blood Coagulation Factor IX mediated by Adeno-Associated Viral Vector", Nature Medicine, vol. 5, No. 1, Jan. 1999, 56-63.
Kafri, et al., "Sustained Expression of Genes Delivered Directly Into Liver and Muscle by Lentiviral Vectors", Nature Genetics, vol. 17, No. 3, Nov. 1997, 314-317.
Kreso, et al., "Variable Clonal Repopulation Dynamics Influence Chemotherapy Response in Colorectal Cancer", Science, vol. 339, No. 6119, Dec 13, 2012, 7 pages.
Kurihara, et al., "Selectivity of a Replication-Competent Adenovirus for Human Breast Carcinoma Cells Expressing the MUC1 Antigen", Journal of Clinical Investigation, vol. 106, No. 6, Sep. 15, 2000, 763-771.
Lee, et al., "Selective Activation of Ceruloplasmin Promoter in Ovarian Tumors: Potential use for Gene Therapy", Cancer Research, vol. 64, Mar. 1, 2004, 1788-1793.
Lewis, et al., "Human Immunodeficiency Virus Infection of Cells Arrested in the Cell Cycle", The EMBO Journal, vol. 11, No. 8, Aug. 1992, 3053-3058.
Li, et al., "Assessment of Recombinant Adenoviral Vectors for Hepatic Gene Therapy", Human Gene Therapy, vol. 4, No. 4, Aug. 1, 1993, 403-409.
Liu, et al., "Establishment of Patient-Derived Tumor Xenograft Models of Epithelial Ovarian Cancer for Preclinical Evaluation of Novel Therapeutics", Clinical Cancer Research, vol. 23, No. 5, Mar. 1, 2017, 20 pages.
O'Hare, et al., "Transformation of Mouse Fibroblasts to Methotrexate Resistance by A Recombinant Plasmid Expressing a Prokaryotic Dihydrofolate Reductase", Proceedings of the National Academy of Sciences, vol. 78, No. 3, Mar. 1981, 1527-1531.
Onodera, et al., "Development of Improved Adenosine Deaminase Retroviral Vectors", Journal of Virology, vol. 72, No. 3, Mar. 1998, 1769-1774.
Peterson, et al., "Ascites Analysis by a Microfluidic Chip Allows Tumor-Cell Profiling", Proceedings of the National Academy of Sciences of the United States of America,, Dec. 2, 2013, E4978-E4986.
Piccini, et al., "Vaccinia Virus as an Expression Vector", Methods in Enzymology, vol. 153, 1987, 545-563.
Rodriguez, et al., "Prostate Attenuated Replication Competent Adenovirus (ARCA) CN706: A Selective Cytotoxic for Prostate-Specific Antigen-Positive Prostate Cancer Cells", Cancer Research, vol. 57, No. 13, Jul. 1, 1997, 2559-2663.
Sawen, et al., "Mitotic History Reveals Distinct Stem Cell Populations and Their Contributions to Hematopoiesis", Cell Reports, vol. 14, No. 12, Mar. 29, 2016, 2809-2818.
Shackleford, et al., "Construction of a Clonable, Infectious, and Tumorigenic Mouse Mammary Tumor Virus Provirus and a Derivative Genetic Vector", Proceedings of the National Academy of Sciences of the United States of America, vol. 85, Dec 1988, 9655-9659.
Snyder, et al., "Correction of Hemophilia B in Canine and Murine Models using Recombinant Adeno-Associated Viral Vectors", Nature Medicine, vol. 5, No. 1, Jan. 1999, 64-70.
Takebe, et al., "SROT Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, Jan. 1988, 466-472.
Wang, et al., "Sustained Correction of Bleeding Disorder in Hemophilia B Mice by Gene Therapy", Proceedings of the National Academy of Sciences of the United States of America, vol. 96, No. 7, Mar. 30, 1999, 3906-3910.
Warnock, et al., "Introduction to Viral Vectors", Methods in Molecular Biology, vol. 737, 2011, 1-25.

* cited by examiner

Lineage: TCTGTCAGTGTCACAGTCACTCTCACTGTC

SEQ ID NO: 1

EXPRESSED BARCODE LIBRARIES AND USES THEREOF

CROSS-REFERENCE TO RELATED APPLICATIONS

This application claims the benefit of U.S. Provisional Application No. 62/728,701, filed Sep. 7, 2018. The entire contents of the above-identified application are hereby fully incorporated herein by reference.

STATEMENT REGARDING FEDERALLY SPONSORED RESEARCH

This invention was made with government support under Grant No.(s) HG006193 awarded by the National Institutes of Health. The government has certain rights in the invention.

REFERENCE TO AN ELECTRONIC SEQUENCE LISTING

The contents of the electronic sequence listing (BROD_4790US_ST25.txt"; Size is 534 bytes and it was created on Oct. 28, 2020) is herein incorporated by reference in its entirety.

TECHNICAL FIELD

The subject matter disclosed herein is generally directed to barcoded nucleic acids for uncovering metabolic adaptations of cancer persister cells.

BACKGROUND

Despite a favorable initial response, many cancer patients will experience recurrence of disease within months to years of diagnosis. It is thought that recurrence arises as a result of the growth of residual cancer cells that remain after treatment. The ability of a subset of cells to survive is attributed frequently to genetic heterogeneity. However, in many types of cancers (e.g., ovarian cancer), the recurrent disease remains sensitive to first-line therapy, suggesting a non-Darwinian process. For example, persisters are a subpopulation of transiently drug-tolerant cells that are able to survive cytotoxic exposure to targeted therapy of chemotherapy through reversible, non-mutational mechanisms. There is a need for multi-functional tools to study the mechanisms of dynamic cellular processes such as non-genetic resistance that will allow the de-convolution and uncovering of various contributing factors. The present technology addresses these needs.

SUMMARY

Disclosed herein are expressed barcode libraries and uses thereof.

In one aspect, the present technology provides nucleic acid molecules comprising: (i) a molecular barcode having a variable sequence operably linked to a promoter, (ii) a polynucleotide comprising a first reporter gene operably linked to a constitutive promoter, and (iii) a polynucleotide comprising a second reporter gene operably linked to an inducible promoter system.

In some embodiments, the molecular barcode, the polynucleotide comprising a first reporter gene, and the polynucleotide comprising a second reporter gene linked to each other consecutively in any order.

In some embodiments, the first reporter gene encodes a fluorescent protein. In some embodiments, the fluorescent protein is selected from the group consisting of: an mNeon protein, a green fluorescent protein (GFP), a red fluorescent protein (RFP), an mCherry protein, a tdTomato protein, an E2 Crimson protein, a Cerulean protein, an mBanana protein. In some embodiments, the first reporter gene encodes an mNeon protein.

In some embodiments, the first reporter gene further comprises a nuclear localization signal (NLS).

In some embodiments, the constitutive promoter operably linked to the first reporter gene is selected from the group consisting of: phosphoglycerate kinase 1 (PGK) promoter, simian virus 40 (SV40) promoter, cytomegalovirus (CMV) promoter, ubiquitin C (UBC) promoter, and elongation factor-1 alpha (EF1A) promoter.

In some embodiments, the molecular barcode and the polynucleotide comprising the first reporter gene are operably linked to the same promoter. In some embodiments, the molecular barcode and the polynucleotide comprising the first reporter gene are operably linked to separate promoters.

In some embodiments, the first reporter gene and/or the molecular barcode are linked to a tandem gene expression element. In some embodiments, the tandem gene expression element is an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A). In some embodiments, the tandem gene expression element is T2A.

In some embodiments, the second reporter gene encodes a fluorescent protein. In some embodiments, the fluorescent protein is selected from the group consisting of: an mNeon protein, a green fluorescent protein (GFP), a red fluorescent protein (RFP), an mCherry protein, a tdTomato protein, an E2 Crimson protein, a Cerulean protein, an mBanana protein.

In some embodiments, the first reporter gene and the second reporter gene encode fluorescent proteins that are distinguishable from each other.

In some embodiments, detection of the gene product of the second reporter gene is indicative of the proliferative status of the cell.

In some embodiments, the gene product of the second reporter gene comprises a histone binding protein. In some embodiments, the hi stone binding protein is H2B. In some embodiments, the hi stone binding protein is fused to a fluorescent protein.

In some embodiments, the inducible promoter operably linked to the second reporter gene is selected from the group consisting of: a light inducible promoter, a chemically inducible promoter, and an energy inducible promoter.

In some embodiments, the energy inducible promoter is inducible by using electromagnetic radiation, sound energy, chemical energy, or thermal energy.

In some embodiments, the light inducible promoter is a phytochrome, a Light-Oxygen-Voltage (LOV) domain, or a cryptochrome.

In some embodiments, the chemically inducible promoter is a tetracycline inducible promoter. In some embodiments, the Tet inducible promoter is a tetracycline-responsive element (TRE). In some embodiments, the nucleic acid molecule further comprises a Tet-on transactivator. In some embodiments, the Tet-on transactivator is operably linked to the constitutive promoter operably linked to the first reporter gene. In some embodiments, the transactivator is expressed in the forward direction from the constitutive promoter and the second reporter gene is expressed from the TRE promoter in the reverse orientation.

In some embodiments, the molecular barcode has a length of 10-15, 15-20, 20-25, 35-30, or 30-35 nucleotides.

In some embodiments, the molecular barcode comprises a semi-random sequence.

In some embodiments, the molecular barcode further comprises one or more amplification sequences.

In one aspect, the present technology provides a vector comprising the nucleic acid molecules of the present disclosure. In some embodiments, the vector is a plasmid. In some embodiments, the vector is a viral vector. In some embodiments, the viral vector is selected from the group consisting of: herpes simplex virus (HSV) vectors, vaccinia virus vectors, cytomegalovirus vectors, moloney murine leukemia virus vectors, adenovirus vectors, adeno-associated virus vectors, retrovirus vectors, and lentivirus vectors.

In one aspect, the present technology provides cells comprising the nucleic acid molecules and/or vectors of the present disclosure. In some embodiments, the cell is a cancer cell.

In one aspect, the present technology provides a population of nucleic acid molecules according to the present disclosure, wherein there are at least 50,000 different molecular barcode sequences in the population.

In one aspect, the present technology provides a vector library comprising a population of nucleic acid molecules of the disclosure.

In some embodiments, the vectors are plasmids. In some embodiments, the vectors are viral vectors. In some embodiments, the viral vectors are selected from the group consisting of: herpes simplex virus (HSV) vectors, vaccinia virus vectors, cytomegalovirus vectors, moloney murine leukemia virus vectors, adenovirus vectors, adeno-associated virus vectors, retrovirus vectors, and lentivirus vectors.

In one aspect, the present technology provides a population of cells comprising (i) a population of nucleic acid molecules of the present disclosure, or (ii) a vector library of the present disclosure. In some embodiments, the cells are cancer cells. In some embodiments, the cells are derived from cell lines or stable cell cultures.

In one aspect, the present technology provides a method of genetically barcoding a cell, a population of cells, or a culture of cells, comprising: (i) providing a cell, a population of cells or a culture of cells; (ii) providing at least one nucleic acid molecule according to the present disclosure, wherein the at least one nucleic acid is contained within a vector capable of stably transfecting, transducing, or infecting the cell; and (iii) transfecting, transducing, or infecting the cell, population of cells, or culture of cells with the vector, leading to the integration of an individual molecular barcode into the genomic DNA of the cell or each cell of the population or culture of cells, thereby genetically barcoding the cell, population of cells, or culture of cells.

In one aspect, the present technology provides a method of simultaneously profiling the cell lineage and transcriptional state of single cells in a population of cells comprising: (i) stably transfecting, transducing, or infecting a population of cells with a vector library according to the present disclosure; (ii) allowing for transcription of the molecular barcode, the first reporter gene, and the second reporter gene; (iii) profiling the transcriptome of single cells in the population of cells by single cell sequencing; and (iv) associating the lineage of a single cell within the population with its transcriptional profile based on the expression of the molecular barcode.

In one aspect, the present technology provides a method of identifying genes associated with tumor dormancy comprising: (i) stably transfecting, transducing, or infecting a population of cells with a vector library according to the present disclosure, wherein the detection of the gene product of the second reporter gene is indicative of the proliferative status of the cell; (ii) propagating and dividing the cells into identical control and treatment replicate groups; (iii) profiling the transcriptome and lineage of single cells in the control replicate group; (iv) treating the treatment replicate group with a cancer therapeutic; (iv) profiling the transcriptome and lineage of single cells in the treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v) and (vi) to identify genes associated with tumor dormancy. In some embodiments, the method further comprises measuring the dilution of gene product of the second reporter over time, wherein the dilution is indicative of proliferative history.

In one aspect, the present technology provides a method of identifying genes associated with stem-cell like treatment-resistant cancer cells comprising: (i) stably transfecting, transducing, or infecting a population of cells with a vector library according to the present disclosure; (ii) propagating and dividing the cells into identical control and treatment replicate groups; (iii) profiling the transcriptome and lineage of single cells in the control replicate group; (iv) treating the treatment replicate group with a cancer therapeutic; (v) profiling the transcriptome and lineage of single cells in the treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v) and (vi) to identify genes associated with stem-cell like treatment-resistant cancer cells.

BRIEF DESCRIPTION OF THE DRAWINGS

FIG. 1A shows representative fluorescence images of platinum-sensitive relapse of OVCAR3 H2B-GFP cells. FIGS. 1B-1E show relapse dynamics. Length of drug treatments are indicated as red shaded areas within the graphs. FIG. 1B shows platinum-sensitive relapse in a patient (CA125 data obtained from Bowtell et al., Nat Rev Cancer 15:668-79 (2015)). FIG. 1C shows in vitro carboplatin-sensitive relapse (6.25 μM treatment) in the OVCAR3 H2B-GFP model. FIG. 1D shows in vitro cisplatin-sensitive relapse (50 μM treatment) in the OVCAR3 H2B-GFP model. FIG. 1E shows variability in lag phase length in response to cisplatin treatment (relapse pattern of two independent wells is shown).

FIG. 3A shows a schematic of H2B-mCherry label dilution over time following dox administration and removal. FIG. 3B shows representative fluorescence microscopy images of cells transduced with the Watermelon vector and grown in dox-containing media. Cells express both nuclear fluorescent markers. FIG. 3C shows the quantification of mCherry positive cells in the dox-chase period. Cells transduced with the Watermelon vector were exposed to dox for 48 hours prior to starting the experiment. The percentage of mCherry-positive cells at the time of measurement is indicated above each bar. The positive cells in the last time point represent dormant cells. FIG. 3D shows a fluorescence microscopy image of cells two weeks after dox chase. A dormant cell is shown.

FIG. 4A shows a schematic of a lineage tracing experiment. FIG. 4B shows a t-distributed stochastic neighbor embedding (tSNE) plot of transcriptome analysis of 49 cells transduced with the Watermelon library in a pilot experiment. FIG. 4C shows a tSNE plot of transcriptome analysis of 9,355 Watermelon-transduced cells. Marked in red are cells where lineage information was successfully obtained from single cell data.

FIG. 6A shows a schematic for obtaining Watermelon-transduced PC-9 cells. FIGS. 6B and 6C show the sensitivity of Watermelon-transduced PC-9 cells, as measured by the number of mCherry objects, to gefitinib and osimertinib (EGFR-TKIs), at varying concentrations. FIG. 6D shows the response of Watermelon-transduced PC9 cells to dox induction, as measured by fluorescence microscopy and FACS analysis.

FIG. 7A shows a schematic of the experimental design. FIG. 7B shows the percentages of lineage barcodes recovered in each treatment group. FIG. 7C shows the tSNE analysis of the transcriptome data of cells in the different treatment groups. The samples cluster by time and not by drug.

Figure 1A:
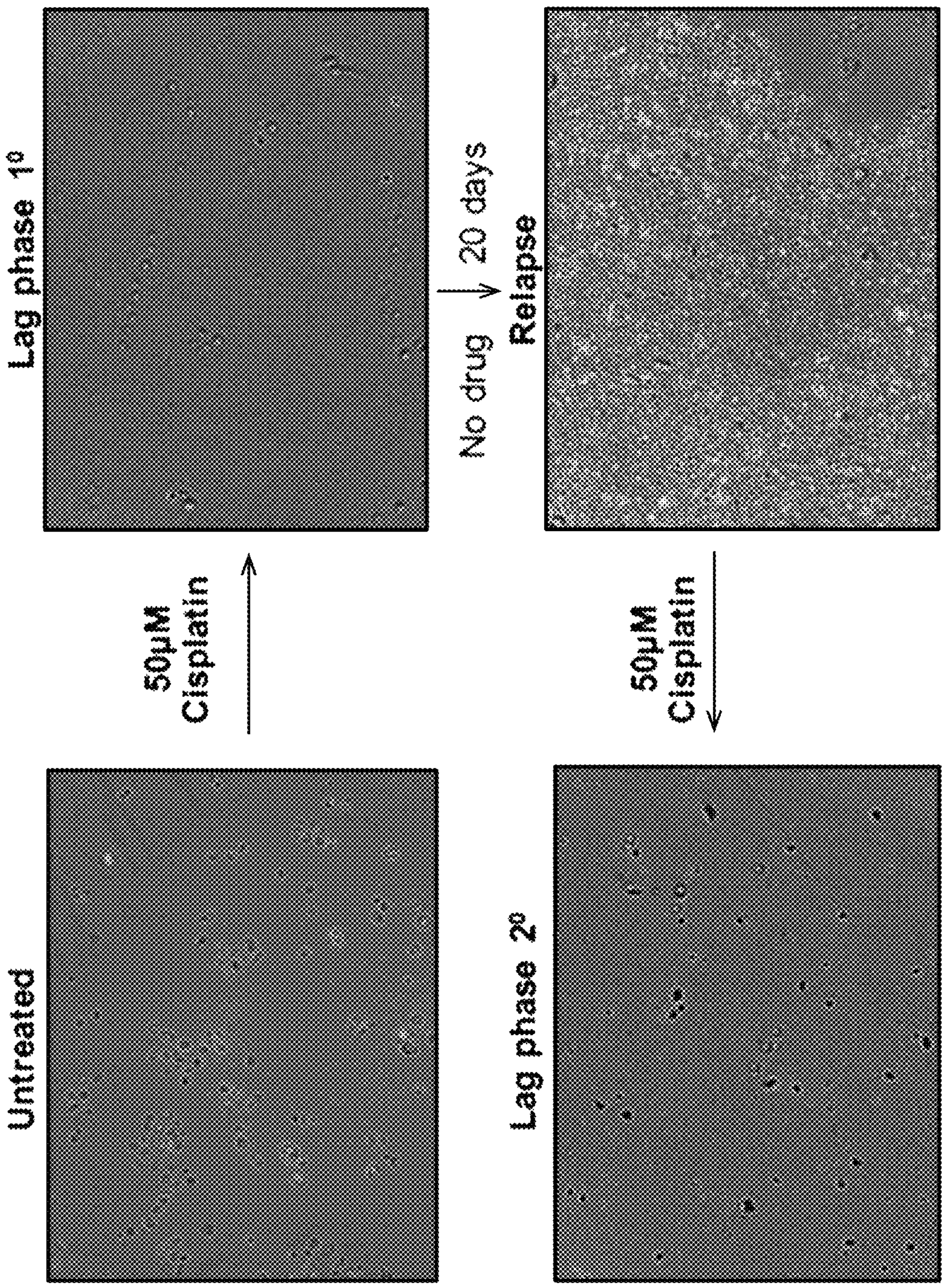
FIGS. 1A-1E show the in vitro modeling of non-inherited drug resistance.

The figures herein are for illustrative purposes only and are not necessarily drawn to scale.

DETAILED DESCRIPTION

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Throughout this disclosure, various publications, patents and published patent specifications are referenced by an identifying citation. The disclosures of these publications, patents and published patent specifications are hereby incorporated by reference in their entireties into the present disclosure to more fully describe the state of the art to which this disclosure pertains.

Technical and scientific terms used herein have the meanings commonly understood by one of ordinary skill in the art to which the present disclosure pertains, unless otherwise defined.

As used herein, the singular forms "a," "an," and "the" designate both the singular and the plural, unless expressly stated to designate the singular only.

As used herein, "and/or" refers to and encompasses any and all possible combinations of one or more of the associated listed items, as well as the lack of combinations when interpreted in the alternative ("or").

As used herein, the terms "administer," "administration," or "administering" refer to (1) providing, giving, dosing and/or prescribing, such as by either a health professional or his or her authorized agent or under his direction, and (2) putting into, taking or consuming, such as by a health professional or the subject.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells, at least about 10,000 cells, at least about 100,000 cells, at least about 1×106 cells, at least about 1×107 cells, at least about 1×108 cells, at least about 1×109 cells, at least about 1×1010 cells, at least about 1×1011 cells, at least about 1×1012 cells, or more cells expressing similar or different phenotypes.

As used herein, "complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, a "host cell" is a cell that is used to receive, maintain, reproduce and amplify a nucleic acid molecule of the present technology or a vector comprising a nucleic acid molecule of the present technology.

As used herein "hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, "operably linked" with reference to nucleic acid sequences, regions, elements or domains means that the nucleic acid regions are functionally related to each other. For example, a nucleic acid encoding a first polypeptide is operably linked to nucleic acid encoding a second polypeptide and the nucleic acids are transcribed as a single mRNA transcript. In another example, a promoter can be operably linked to nucleic acid encoding a polypeptide, whereby the promoter regulates or mediates the transcription of the nucleic acid.

As used herein, the term "polynucleotide," or "nucleic acid molecule," or "nucleic acid" refer to a biopolymer that comprises one or more nucleotide monomers (natural or non-natural) covalently bonded in a chain. In some embodiments, a polynucleotide can have a sequence comprising a genomic nucleic acid sequence. In other embodiments, a polynucleotide can have an artificial sequence (e.g., a sequence not found in genomic nucleic acids). A polynucleotide can comprise genomic nucleic acid sequence and/or an artificial sequence. An artificial sequence may or may not contain non-natural nucleotides.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "subject" denotes any mammal, including humans.

A cell has been "transformed," "transduced," or "transfected" by a nucleic acid molecule when such genetic construct(s) has been introduced inside the cell, for example, as a complex with transfection reagents or packaged in viral particles. The transforming nucleic acid molecule may or may not be integrated (covalently linked) into the genome of the cell. In prokaryotes, yeast, and mammalian cells for example, the transforming nucleic acid molecule may be maintained on an episomal element such as a plasmid. With respect to eukaryotic cells, a stably transformed cell is one in which the transforming nucleic acid molecule has become integrated into a host cell chromosome or is maintained extra-chromosomally so that the transforming nucleic acid molecule is inherited by daughter cells during cell replication. In some instances, the transformed cells acquire a single nucleic acid molecule. Such a stably transduced eukaryotic cell is able to establish cell lines or clones comprised of a population of daughter cells containing the nucleic acid molecule and labeled with the clonal barcode specific for that clone.

As used herein, a "vector" refers to a DNA molecule used as a vehicle to clone and transfer foreign genetic material, e.g., a nucleic acid molecule of the present technology, into a cell. Examples of vectors include plasmids, viruses, cosmids and artificial chromosomes. Vectors finding use in embodiments of the present technology may be employed in linear or circular form and may be either RNA or DNA, and may be either single- or double-stranded form, as desired.

As used herein, a vector also includes "virus vectors" or "viral vectors." Viral vectors are engineered viruses that are operatively linked to exogenous nucleic acid molecules to transfer (as vehicles or shuttles) the exogenous nucleic acid molecules into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

General Overview

Despite favorable initial response to platinum chemotherapy, the majority of patients with high-grade serous ovarian cancer (HGSOC) will develop recurrent disease and succumb to it within 5 years of diagnosis (Bowtell et al., Nat Rev Cancer 15:668-79 (2015)). Initial recurrence is frequently platinum-sensitive and women can respond to multiple lines of platinum-based chemotherapy before eventually developing platinum-refractory disease. While there has been much progress in characterizing the pathways that contribute to stable platinum-based drug resistance, the mechanisms underlying early reversible resistance remain largely unknown. As most patients exhibit reversible resistance before developing a stable one, early non-genetic resistance remains a largely unexplored therapeutic window for inhibiting or delaying the onset of stable drug resistance. Thus, there is a need for multi-functional tools to study the mechanisms of non-genetic resistance by de-convoluting and uncovering the various factors contributing to platinum-sensitive relapse.

Recurrent disease is broadly classified into two groups: platinum-resistant and platinum-responsive cancer (Giornelli, Springerplus 5:1197 (2016)). Platinum-resistant relapse is defined by the lack of measurable clinical response to a rechallenge with the same chemotherapy and is usually attributed to the selection of resistant clones with genetic alterations that promote survival in the presence of the drug. Indeed, multiple studies have associated alterations in genes involved in drug-DNA binding, drug transporter and DNA damage pathways with therapeutic failure (Galluzzi et al., Oncogene 31:1869-83 (2012)). Although most patients will eventually develop chemoresistance, the majority of women who relapse will at least initially respond to platinum-based chemotherapies. This reversible resistance is not consistent with a simple Darwinian model of selection of genetically resistant clones, as cells that survive the initial treatment give rise to a chemoresponsive progeny.

One of the earliest mechanisms suggested to explain reversible non-genetic resistance is tumor dormancy, defined as a condition in which tumor cells stop dividing and remain quiescent (Aguirre-Ghiso, Nat Rev Cancer 7:834-46 (2007)). According to this theory, upon initial treatment, the bulk of the tumor will die and only non-dividing cells that are less vulnerable to chemotherapy will survive. Recurring disease is thought to arise from cells that have exited the growth-arrested state and resumed proliferation. As these 'awakening' cells have never been selected to withstand the insults of chemotherapy, they are not expected to harbor any specific resistance-conferring alterations (Chien et al., Front Oncol 3:251 (2013)). For example, in colorectal cancer, the chemosensitivity of individual tumor cells within a uniform genetic lineage was dependent on their proliferative state (Kreso et al., Science 339:543-8 (2013)). Similarly, quiescent squamous cell carcinoma (SCC) cells exhibit increased tumorigenic potential and decreased DNA damage in response to chemotherapy compared to cycling cells (Brown et al., Cell Stem Cell 21:650-64 e8 (2017)).

An alternate hypothesis to explain platinum-sensitive recurrence is the presence of putative ovarian cancer (OC) stem cells (Lupia & Cavallaro, Mol Cancer 16:64 (2017)). Agarwal and Kaye proposed that while the majority of tumor cells are sensitive to treatment, there is a small clonal population that is chemoresistant (Agarwal & Kaye Nat Rev Cancer 3:502-16 (2003)). Therefore, upon completion of chemotherapy, the remaining stem-like cells can regrow and regenerate the rapidly proliferating chemosensitive population. This model is supported by the observed increase in stem cell markers in recurrent tumors compared to matched primary ovarian tumors (Steg et al. Clin Cancer Res 18:869-81 (2012)). Notably, a central pillar of this theory is the ability of the surviving stem cells to generate a disease which recapitulates the sensitivity and heterogeneity of the original tumor. Indeed, ALDH+/CD133+ stem-like chemoresistant cells were able to generate ALDH+/− CD133+/− chemosensitive tumors when transplanted in mice (Silva et al. Cancer Res 71:3991-4001 (2011)).

Recently, a new model has emerged to explain drug sensitive relapse: the jackpot model. This model posits that stochastic shifts in cell state can render a cell resistant to treatment in a given time point (Cohen et al. Science 322:1511-6 (2008)). This transient resistant state is not lineage specific and can occur in proliferative cells. The interconversion between the two distinct probabilistic phenotypes is thought to be due to randomness in biochemical processes involving transcription and translation, such as transcriptional bursts. In melanoma, for example, where patients who relapse after BRAF inhibitor treatment are frequently re-challenged with the same drug (Schreuer et al. Lancet Oncol 18:464-72 (2017)), it was shown that stochastic expression of EGFR and AXL can lead to resistance to vemurafenib (Shaffer et al. Nature 546:431-35 (2017)). Without wishing to be bound by theory, the comparable pattern of relapse observed in OC and melanoma may be driven by a similar underlying mechanism.

Importantly, the three mechanisms described above (tumor dormancy, stem cell-like population and stochastic cell state shifts) are not mutually exclusive. In various tumor types, cancer stem cells were found to be mostly quiescent or to possess a very slow cycling rate (Chen et al. Stem Cells Int 2016:1740936 (2016)). In OC, stem-like CD24-positive cells proliferated at a significantly lower rate than CD24-negative cells (Gao et al. Oncogene 29:2672-80 (2010)). Consistent with this finding, chemoresistant cells arrested at G0/G1 expressed high levels of stem cell markers (Zhou et al. Mol Med Rep 10:2495-504 (2014)). Without wishing to be bound by theory, extrinsic environmental factors, such as nutrient deprivation and hypoxia, can induce cell cycle arrest that also promotes stem-like features. Further, because transcriptional noise affects all genes in the genome, it is also plausible that a stochastic high expression of a resistance-conferring gene, such as a multi drug-transporter, will render some cells transiently resistant to treatment.

Currently, an inability to quantify the relative contribution of each of the above factors to platinum-sensitive relapse, together with the scarcity of well characterized experimental non-genetic relapse models, have hampered the development of therapies that target this crucial stage of the disease. To address this urgent need, exemplary experimental non-genetic relapse models and novel approaches of single-cell (SC) lineage-tracing in an exemplary platinum-sensitive relapse model are described. By combining time-lapse imaging, SC sequencing and mathematical models, new relapse-associated cancer vulnerabilities can be identified.

It is demonstrated herein that nucleic acid molecules encoding transcribed molecular barcodes are useful in methods of de-convoluting the factors contributing to platinum-sensitive relapse in a HGSOC relapse cell line model. An HGSOC relapse cell line model was generated and transduced with an expressed lentiviral barcode library, leading to the integration of individual barcodes into the genomic DNA of each cell, resulting in a founder population in which almost every cell has a different DNA barcode and an associated unique transcript. Unlike existing barcoding methods that enable the tracking of multiple cancer cells solely at the DNA level (Bhang et al. Nat Med 21:440-8 (2015)), the present technology provides a barcoding scheme comprising transcribed barcodes. The transcribed barcodes allow one to map the lineage to the transcriptional profile of a cell.

Described herein are novel nucleic acid molecules encoding transcribed molecular barcodes, and vectors, vector libraries, and cells comprising the nucleic acid molecules, and uses thereof. Generally, the nucleic acid molecules comprise a molecular barcode having a variable sequence operably linked to a promoter and one or more polynucleotides comprising one or more reporter genes. The compositions and methods described herein are useful for simultaneously mapping the genetic lineage and transcriptional profile of a cell and are useful for studying any dynamic cellular or molecular pathway that could benefit from mapping the genetic lineage to the transcriptional profile of a cell in a population of cells. In an exemplary proof-of-concept embodiment, by simultaneously tracing the lineage as well as the transcriptional and proliferative state of each cell in the population in a well characterized HGSOC relapse system, the role of specific lineages and transient cell states in response to platinum-sensitive relapse was assessed.

The transcribed barcodes of the present technology can be combined with one or more additional reporter functions to study any dynamic cellular and molecular pathway in a population of cells. The pathways include, but are not limited to, response to drug treatment, non-inherited drug resistance, tumor dormancy, migration and metastatic seeding, response to epithelial-mesenchymal transition (EMT), response to stress, response to nutrient deprivation, response to hypoxia, identification of stem-cell like markers, identification of markers determining length of lag phase and likelihood of relapse after drug treatment, etc. (e.g., in cancer cells, cancer cell lines, tumor models, PDX tumor models, etc.). In some embodiments, the one or more reporter functions allow the use of imaging-based approaches or flow-cytometry to further monitor a desired feature (e.g., live/dead analysis, proliferation status, etc.).

Nucleic Acid Molecules of the Present Technology

The present technology provides nucleic acid molecules comprising molecular barcodes having a variable sequence operably linked to a promoter and one or more polynucleotides encoding one or more reporter genes. In some embodiments, the nucleic acid molecules comprise a molecular barcode having a variable sequence operably linked to a promoter, a polynucleotide comprising a first reporter gene, and a polynucleotide comprising a second reporter gene.

The nucleic acid molecules of the present technology are modular and the molecular barcode and the one or more reporter genes may be consecutively linked to each other in any order. In some embodiments, the nucleic acid molecules comprise, from 5' to 3', a molecular barcode and a reporter gene. In some embodiments, the nucleic acid molecules comprise, from 5' to 3', a molecular barcode, a polynucleotide comprising a first reporter gene, and a polynucleotide comprising a second reporter gene. In some embodiments, the molecular barcode is flanked on either side by polynucleotides comprising reporter genes.

In some embodiments, the molecular barcode is operably linked to its own promoter. In some embodiments, the promoter is a constitutive promoter. In some embodiments, the promoter is an inducible promoter. In some embodiments, the molecular barcode is co-transcribed with a reporter gene. In some embodiments, the molecular barcode and a first reporter gene are operably linked to the same promoter. In some embodiments, the molecular barcode and a first reporter gene are operably linked to a constitutive promoter. In some embodiments, the molecular barcode and a first reporter gene are operably linked to an inducible promoter. In some embodiments, the nucleic acid molecules of the present technology further comprise a second reporter gene. In some embodiments, the second reporter gene is operably linked to its own promoter. In some embodiments, the second reporter gene is operably linked to a constitutive promoter. In some embodiments, the second reporter gene is operably linked to an inducible promoter. In some embodiments, the molecular barcode and a first reporter gene are operably linked to a constitutive promoter and a second reporter gene is operably linked to an inducible promoter.

Promoters are sequences located around the transcription or translation start site, typically positioned 5' of the translation start site. Promoters usually are located within 1 Kb of the translation start site, but can be located further away, for example, 2 Kb, 3 Kb, 4 Kb, 5 Kb or more, up to and including 10 Kb. Constitutive promoters are known in the art and include but are not limited to phosphoglycerate kinase 1 (PGK) promoter, simian virus 40 (SV40) promoter, cytomegalovirus (CMV) promoter, ubiquitin C (UBC) promoter, and elongation factor-1 alpha (EF1A) promoter.

In some embodiments, one or more modules of the nucleic acid molecules of the present technology, i.e., the molecular barcode, the first reporter gene, or the second reporter gene, etc. are part of an inducible system. The inducible nature of the system would allow for spatiotemporal control of barcode or reporter gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc.), or light inducible systems (Phytochrome, LOV domains, or cryptochrome). In one embodiment, one or more modules of the nucleic acid molecules of the present technology may be a part of a Light Inducible Transcriptional Effector (LITE) to direct changes in transcriptional activity in a sequence-specific manner. The components of a LITE may include a light-responsive cryptochrome heterodimer (e.g., from *Arabidopsis thaliana*), and a transcriptional activation/repression domain. In some embodiments, an inducible promoter is a light inducible promoter, a chemically inducible promoter, and an energy inducible promoter. In some embodiments, the light inducible promoter is a phytochrome, a Light-Oxygen-Voltage (LOV) domain, or a cryptochrome. In some embodiments, the promoter is a tetracycline or doxycycline inducible promoter (e.g., a tetracycline-responsive element (TRE)). In some a tetracycline inducible system further comprises a Tet-on transactivator.

In some embodiments, the Tet-on transactivator is operably linked to the constitutive promoter operably linked to the first reporter gene. In some embodiments, the transactivator is expressed in the forward direction from the constitutive promoter and the second reporter gene is expressed from the TRE promoter in the reverse orientation.

In some embodiments, any of the modules of the nucleic acids of the present technology, i.e., the molecular barcode, the first reporter gene, the second reporter gene, etc. may be operably linked to additional regulatory elements such as enhancers, transactivators, tandem gene expression elements, etc. In general, regulatory elements include a cis-acting nucleotide sequence that influences expression, positively or negatively, of an operatively linked gene. Regulatory regions include sequences of nucleotides that confer inducible (i.e., require a substance or stimulus for increased transcription) expression of a gene. When an inducer is present or at increased concentration, gene expression can be increased. Regulatory regions also include sequences that confer repression of gene expression (i.e., a substance or stimulus decreases transcription). When a repressor is present or at increased concentration gene expression can be decreased. Regulatory regions are known to influence, modulate or control many in vivo biological activities including cell proliferation, cell growth and death, cell differentiation and immune modulation. Regulatory regions typically bind to one or more trans-acting proteins, which results in either increased or decreased transcription of the gene. Particular examples of gene regulatory regions are promoters and enhancers. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more. Enhancer elements, include but are not limited to WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

Regulatory elements also include, but are not limited to, sequences that facilitate translation, splicing signals for introns, maintenance of the correct reading frame of the gene to permit in-frame translation of mRNA and, stop codons, leader sequences and fusion partner sequences, tandem gene expression elements (such as but not limited to internal ribosomal entry sites (IRES), foot-and-mouth disease virus 2A peptide (F2A), equine rhinitis A virus 2A peptide (E2A), porcine teschovirus 2A peptide (P2A) or Thosea asigna virus 2A peptide (T2A)) for the creation of multigene, or polycistronic, messages, transcription termination signals (such as polyadenylation signals and poly-U sequences), and can be optionally included in the nucleic acid molecules of the present technology. Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types. Regulatory elements may also direct expression in a temporal-dependent manner, such as in a cell-cycle dependent or developmental stage-dependent manner, which may or may not also be tissue or cell-type specific. In some embodiments, the nucleic acid molecules of the present technology may comprise one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and HI promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter.

Figure 2:
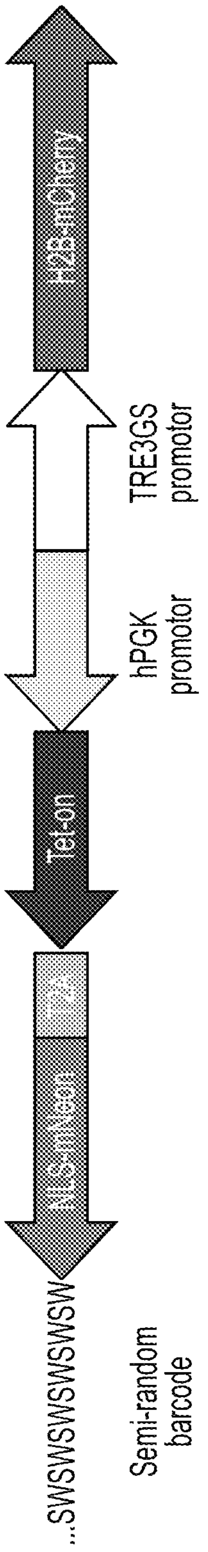
FIG. 2 shows a schematic of the features of the Watermelon vector. The vector encodes an inducible H2B-mCherry reporter gene, a tetracycline-controlled trans-activator, a constitutive NLS-mNeon fluorescent marker, and a 30bp semi-random barcode.

A schematic of an exemplary nucleic acid molecule of the present technology is shown in FIG. 2.

Molecular Barcodes

The present technology provides nucleic acid molecules comprising molecular barcodes having a variable sequence operably linked to a promoter. The term "barcode" or as used herein, refers to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

Unlike existing barcoding methods that enable the tracking of multiple cancer cells solely at the DNA level, the present technology provides a barcoding scheme comprising transcribed barcodes. The transcribed barcodes allow one to map the lineage to the transcriptional profile of a cell. The barcodes allow the labeling of individual members of a starting population of cells with specific sequences. These specific sequences can be used to measure the clonal abundance before and after a treatment. Since the barcodes of the present technology are transcribed, the expressed barcodes allow recovery of the transcriptional profile of individual members of a starting population of cells in addition to information about the genetic lineage of the individual members.

A molecular barcode refers to a sequence of nucleotides that is used to identify a nucleic acid molecule (or its transcript) as originating from a particular cell. For example, a barcode of the present technology can be used to identify the clonal origin of molecules when the molecules from several cells are combined for processing or sequencing in a multiplexed fashion. A molecular barcode can be located at a certain position within a polynucleotide (e.g., at the 3'-end, 5'-end, or middle of the polynucleotide) and can comprise sequences of any length (e.g., 1-100 or more nucleotides).

In some embodiments, a molecular barcode comprises a random oligonucleotide sequence. A random oligonucleotide sequence can comprise the standard four deoxyribonucleotides (i.e., A, C, G, and T) and refers to a sequence not having a precise definition. In some embodiments, a molecular barcode comprises a semi-random oligonucleotide sequence. In some embodiments, the oligonucleotide sequence is DNA. The term "semi-random barcode sequences," "semi-random barcodes," "semi-random oligonucleotide sequences," or "semi-random sequences" refers to a population of semi-random oligonucleotide sequences each comprising (Xmer)n, wherein Xmer is a 2-mer (i.e., a 2-nucleotide oligonucleotide, also referred to as a "dimer"), a 3-mer (i.e., a 3-nucleotide oligonucleotide, also referred to as "trimer"), 4-mer (i.e., a 4-nucleotide oligonucleotide, also refers to as "tetramer")), 5-mer (i.e., a 5-nucleotide oligonucleotide, also refers to as "pentamer"), or 6-mer (i.e., a 6-nucleotide oligonucleotide, also refers to as "hexamer"), and n is an integer from 2 to 20. Each nucleotide sequence in the population is referred to as "semi-random barcode sequence," "semi-random barcode," "semi-random oligonucleotide sequence," or "semi-random sequence."

In some embodiments, the molecular barcode comprises a semi-random oligonucleotide sequence comprising (Xmer)n, wherein the Xmer is a dimer and n is an integer from 2 to 20. In some embodiments, the Xmer is a dimer of A or T ("W" for weak) and G or C ("S" for strong). Thus, in some embodiments, the molecular barcode comprises "WS" repeats. In some embodiments, the molecular barcode may comprise SW repeats. In some embodiments, n is an integer from 5-10, 10-15, or 15-20. In some embodiments, n is 2, 3, 4, 5, 6, 7, 8, 9, 10, 11, 12, 13, 14, 15, 16, 17, 18, 19, or 20. In some embodiments, n is 15. In some embodiments, the molecular barcode comprises 5-10, 10-15, or 15-20 WS or SW repeats. In some embodiments, the molecular barcode comprises 2, 3, 4, 5, 6, 7, 8, 9, 10, 11, 12, 13, 14, 15, 16, 17, 18, 19, or 20 WS or SW repeats. In some embodiments, the molecular barcode comprises 15 WS or SW repeats. In some embodiments, the molecular barcode comprises 15 WS repeats.

In some embodiments, the molecular barcode may be at least 5, 10, 15, 20, 25, 30, 35, 40, 45, 50, 60, 70, 80, 90, or 100 nucleotides in length. In some embodiments, the molecular barcode may have a length of 5-10, 10-15, 15-20, 20-25, 35-30, or 30-35 nucleotides. In some embodiments, the molecular barcode is at least 10 nucleotides in length. In some embodiments, the molecular barcode is about 5 to about 100, about 5 to about 90, about 5 to about 80, about 5 to about 70, about 5 to about 60, about 5 to about 50, about 10 to about 5, about 5 to about 30, about 5 to about 20, about 10 to about 100, about 10 to about 90, about 10 to about 80, about 10 to about 70, about 10 to about 60, about 10 to about 50, about 10 to about 40, about 10 to about 30, or about 10 to about 20, about 20 to about 30 nucleotides, about 20 to about 35, or about 20 to about 40 nucleotides in length. In some embodiments, the molecular barcode is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, a barcode can comprise one or more pre-defined sequences. In some embodiments, a barcode can comprise artificial sequences, e.g., designed or engineered sequences that are not present in the unaltered (wild-type) genome of a subject. In other embodiments, a barcode can comprise an endogenous sequence, e.g., sequences that are present in the unaltered (wildtype) genome of a subject. In certain embodiments, a barcode can be an endogenous barcode. An endogenous barcode can be a sequence of a genomic nucleic acid, where the sequence is used as a barcode or identifier for the genomic nucleic acid. One or more sequences of the genomic DNA fragment can be an endogenous barcode. Different types of barcodes can be used in combination. For example, an endogenous genomic nucleic acid fragment can be attached to an artificial sequence, which can be used as a unique identifier of the genomic nucleic acid fragment.

The abundance of each barcoded clone can be monitored over time by sequencing the barcodes in the population. In some embodiments, the molecular barcodes further comprise one or more amplification sequences. In some embodiments, all barcodes can be amplified (e.g., by PCR) using the same sets of forward and reverse primers. The abundance of a particular barcode sequence corresponds to the abundance of a specific clone, and lineage tracing is performed via barcode sequencing. In some embodiments, the untranscribed DNA barcodes are sequenced. In some embodiments, the transcribed barcodes are sequenced. The molecular barcodes may further comprise reverse transcription primers, PCR primers, or portions of sequencing adapters to prepare sequencing libraries. The resulting sequencing libraries can be used for sequencing DNA or RNA, including lineage tracing and transcriptome profiling. The amplification primers may be single-stranded.

In some embodiments, the molecular barcodes (including the variable sequence and the amplification primers) comprise deoxyribonucleotides. The deoxyribonucleotides can comprise the standard four nucleotides (i.e., A, C, G, and T), as well as nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids, peptide nucleic acids, and morpholinos. The backbone of the amplification primers can comprise phosphodiester linkages, as well as phosphothioate, phosphoramidite, or phosphorodiamidate linkages.

Population dynamics after a particular treatment (e.g., treatment with a drug, exposure to stress, exposure to hypoxia, exposure to nutrient deprivation, EMT, etc.) can be monitored by measuring barcode abundance among multiple replicate populations. The molecular barcodes may be introduced into any desired host cell population. Host cells may include any suitable cell line (e.g., a cancer cell line or a patient-derived xenograft (PDX) model).

The nucleic acid molecules comprising the molecular barcodes operably linked to a promoter can be introduced into suitable vectors to generate a vector library. A vector library comprises at least 50,000 unique molecular barcode sequences in the population. In some embodiments, a vector library may have at least 100,000, at least 250,000, at least 500,000, at least 750,000, at least 1×106, at least 2×106, at least 3×106, at least 4×106, at least 5×106, at least 1×107, at least 2×107, at least 3×107, at least 4×107, at least 5×107, at least 6×107, or at least 7×107 unique molecular barcode sequences in the population. In some embodiments, a vector library may have at least 1×106 unique molecular barcode sequences in the population.

In some embodiments, the invention provides a population of nucleic acid molecules wherein there are at least 50,000 different molecular barcode sequences in the population.

Reporter Genes

The nucleic acid molecules of the present technology comprise one or more reporter genes. In some embodiments, a reporter gene further comprises a nuclear localization signal (NLS) for nuclear expression of the reporter gene. A number of reporter genes are known in the art and the reporter genes are selected based on the output being measured. For example, one or more reporter genes encodes a fluorescent protein reporter molecule. The fluorescent protein may be constitutively expressed and may be useful for monitoring and evaluating live cell response to a treatment, for example, by live cell imaging. A number of fluorescent proteins are known in the art.

The fluorescent protein may be, but is not limited to, an mNeon protein, a green fluorescent protein (GFP), a red fluorescent protein (RFP), an mCherry protein, a tdTomato protein, an E2 Crimson protein, a Cerulean protein, an mBanana protein, HcRed, DsRed, a cyan fluorescent protein (CFP), a yellow fluorescent protein (YFP), an infrared fluorescent protein (IFP), a far-red fluorescent protein (FFP) or an autofluorescent protein including blue fluorescent protein (BFP). Examples of GFP include, but are not limited to, enhanced GFP (EGFP), NowGFP, Clover, mClover3, and nNeonGreen. Examples of YFP include, but are not limited to, enhanced yellow FP (EYFP) and derivatives thereof. Examples of EYFP derivatives include, but are not limited to, mVenus, mCitrine, sEYFP, and YPet. Examples of BFP include enhanced BFP (EBFP). Examples of RFP include, but are not limited to, mRuby2, mRuby3, mCherry. Examples of CFP include, but are not limited to, mTurquoise2, mCerulean3, mTFP1 and Aquamarine. Examples of IFPs include, but are not limited to, IFP1.4 and iRFP. Examples of FFPs include, but are not limited to, mPlum, eqFP650, an mCardinal. In some embodiments, the fluorescent protein is an mNeon protein. In some embodiments, the nucleic acid molecules of the present technology comprise an NLS-mNeon reporter gene to monitor live cell response to a treatment (e.g., drug treatment, exposure to stress, nutrient deprivation, hypoxia, etc.).

In some embodiments, a reporter gene encodes a reporter molecule that monitors the proliferative state of a cell. For example, any molecule (e.g., protein) that is partitioned equally between sister cells during cell division can serve as a reporter of the proliferative status of the cell. Such reporter molecules are known in the art. In some embodiments, a reporter molecule is a dye. In some embodiments, the reporter molecule is a histone binding protein that partitions equally between sister cells. In some embodiments, the histone binding protein incorporates into chromatin in a replication-independent manner allowing the labeling of non-dividing cells. Examples of histone binding proteins include, but are not limited, to H2B. In some embodiments, the reporter molecule (e.g., histone binding protein) may optionally be fused to a fluorescent protein to allow imaging-based proliferation tracking. The reporter gene may be under the control of a constitutive promoter or under the control of an inducible promoter or under a tissue-specific promoter. When under the control of an inducible promoter, the reporter molecule will partition between sister cells upon a pulse of induction. Further, since transcription of the reporter molecule will be turned off once the inducer is removed, only quiescent or very slowly proliferating cells are expected to retain the reporter molecule long after the induction pulse. In some embodiments, the nucleic acid molecules of the present technology comprise an H2B-mCherry reporter gene to track the proliferative status of a cell.

In some embodiments, the constitutive promoter operably linked to the first reporter gene may include, but is not necessarily limited to, phosphoglycerate kinase 1 (PGK) promoter, simian virus 40 (SV40) promoter, cytomegalovirus (CMV) promoter, ubiquitin C (UBC) promoter, elongation factor-1 alpha (EF1A) promoter, RNA polymerases, pol I, pol II, pol III, T7, U6, H1, retroviral Rous sarcoma virus (RSV) LTR promoter, the dihydrofolate reductase promoter, the β-actin promoter, the phosphoglycerol kinase (PGK) promoter, and the EF1α promoter.

In some embodiments, a reporter gene encodes a reporter molecule that monitors one or more of: proliferative status, cell migration, metastatic seeding, response to EMT, response to stress, response to nutrient deprivation, response to hypoxia, etc.

In some embodiments, a reporter gene is under the control of a promoter that can sense an output of interest. For example, a reporter gene (e.g., a gene encoding a fluorescent protein) may be under the control of a promoter that is responsive to stress, hypoxia, or nutrient deprivation. In some embodiments, a reporter gene (e.g., a gene encoding a fluorescent protein) may be under the control of a promoter that is responsive to EMT. In some embodiments, the promoter is a cancer selective/specific promoters (and or promoter/enhancer sequences) including but not limited to: PEG-PROM, astrocyte elevated gene 1 (AEG-1) promoter (AEG-Prom), survivin-Prom, human telomerase reverse transcriptase (hTERT)-Prom, hypoxia-inducible promoter (HIF-1-alpha), DNA damage inducible promoters (e.g., GADD promoters), metastasis-associated promoters (metalloproteinase, collagenase, etc.), ceruloplasmin promoter (Lee et al., Cancer Res Mar. 1, 2004 64; 1788), mucin-1 promoters such as DF3/MUC1 (see U.S. Pat. No. 7,247,297), HexII promoter as described in US patent application 2001/00111128; prostate-specific antigen enhancer/promoter (Rodriguez et al. Cancer Res., 57: 2559-2563, 1997); α-fetoprotein gene promoter (Hallenbeck et al. Hum. Gene Ther., 10: 1721-1733, 1999); the surfactant protein B gene promoter (Doronin et al. J. Virol., 75: 3314-3324, 2001); MUC1 promoter (Kurihara et al. J. Clin. Investig., 106: 763-771, 2000); H19 promoter as per U.S. Pat. No. 8,034,914; those described in issued U.S. Pat. Nos. 7,816,131, 6,897,024, 7,321,030, 7,364,727, and others; etc., as well as derivative forms thereof. Any promoter that is specific for driving gene expression only in cancer cells, or that is selective for driving gene expression in cancer cells, or at least in cells of a particular type of cancer may be used. The promoter, when operably linked to a gene, functions to promote transcription of the gene only when located within a cancerous, malignant cell, but not when located within normal, non-cancerous cells. The promoter, when operably linked to a gene, may also function to promote transcription of the gene to a greater degree when located within a cancer cell, than when located within non-cancerous cells.

In some embodiments, where the nucleic acid molecules comprise two or more reporter genes that encode fluorescent proteins, the fluorescent proteins are distinguishable from each other, i.e., the fluorescent proteins have distinct absorbance/emission spectra.

Additional examples of reporter genes include, but are not limited to, glutathione-S-transferase (GST), horseradish peroxidase (HRP), chloramphenicol acetyltransferase (CAT) beta-galactosidase, beta-glucuronidase, and luciferase. In some embodiments, pH sensitive molecules such as fluorescent pH dyes can be used as the reporter molecules to monitor fluctuation of intracellular pH. In some embodiments, an ion channel can be used as a reporter molecule to monitor fluctuations in membrane potential and/or intracellular ion concentration. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a millisecond.

In some embodiments, the molecular barcode, the polynucleotide comprising a first reporter gene, and the polynucleotide comprising a second reporter gene are linked to each other consecutively in any order.

In specific embodiments, the molecular barcode and the polynucleotide comprising the first reporter gene are operably linked to the same promoter.

In some embodiments, the molecular barcode and the polynucleotide comprising the first reporter gene are operably linked to the separate promoters.

In some embodiments, the second reporter gene may encode a fluorescent protein, including, but not necessarily limited to, an mNeon protein, a green fluorescent protein (GFP), a red fluorescent protein (RFP), an mCherry protein, a tdTomato protein, an E2 Crimson protein, a Cerulean protein, or an mBanana protein.

In some embodiments, the first reporter gene and the second reporter gene encode fluorescent proteins that are distinguishable from each other.

In some embodiments, detection of the gene product of the second reporter gene is indicative of the proliferative status of the cell.

In some embodiments, the first reporter gene and/or the molecular barcode are linked to a tandem gene expression element, including, but not necessarily limited to, an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A). In specific embodiments, the tandem gene expression element is T2A.

In some embodiments, the gene product of the second reporter gene comprises a histone binding protein. In specific embodiments, the histone binding protein is H2B.

Vectors and Vector Libraries

In one aspect, the present technology also provides vectors and vector libraries comprising the nucleic acid molecules of the disclosure.

A library may refer to a collection of nucleic acid molecules comprising different molecular barcodes that allow for unique identification. The nucleic acid molecules comprising the molecular barcodes operably linked to a promoter can be introduced into suitable vectors to generate a vector library. Within a given library, the number of unique molecular barcodes of differing sequence represented in the library may vary. In some instances, the number of unique molecular barcodes of differing sequence present in the library is a fraction of the number of unique sequences of the library, where the fraction may be 25% or less, such as 20% or less, including 15% or less than the number of unique sequences in the library. In some instances, the number of unique molecular barcodes of differing sequence present in the library is 100 or more, such as 250 or more, e.g., 500 or more, 1000 or more, including 1500 or more, such as 2000 or more, 2500 or more, 3000 or more, 35000 or more, e.g., 5000 or more, including 10,000 or more. In some embodiments, a library comprises at least 50,000 unique molecular barcode sequences in the population. In some embodiments, a library may have at least 100,000, at least 250,000, at least 500,000, at least 750,000, at least 1×106, at least 2×106, at least 3×106, at least 4×106, at least 5×106, at least 1×107, at least 2×107, at least 3×107, at least 4×107, at least 5×107, at least 6×107, or at least 7×107 unique molecular barcode sequences in the population. In some embodiments, a library may have at least 1×106 unique molecular barcode sequences in the population.

The vector may be a plasmid. The vector may be an expression vector. The plasmid may be a mammalian expression vector. The vector may be viral vector. The viral vector may be a herpes simplex virus (HSV) vector, vaccinia virus vector, cytomegalovirus vector, moloney murine leukemia virus vector, adenovirus vector, adeno-associated virus vector, retrovirus vector, or lentivirus vector. The vector may be a lentiviral vector.

Nucleic acid molecules of the present technology can be inserted into delivery vectors and expressed from transcription units within the vectors. The recombinant vectors can be DNA plasmids, non-viral vectors, or viral vectors. Generation of the vector construct can be accomplished using any suitable genetic engineering techniques well known in the art, including, without limitation, the standard techniques of PCR, oligonucleotide synthesis, restriction endonuclease digestion or "seamless cloning", ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). "Seamless cloning" allows joining of multiple fragments of nucleic acids in a single, isothermal reaction (Gibson (2009) Nat Methods 6:343-345; Werner (2012) Bioeng Bugs 3:38-43; Sanjana (2012) Nat Protoc 7:171-192). As will be apparent to one of ordinary skill in the art, a variety of suitable vectors are available for transferring nucleic acids of the present technology into cells. The selection of an appropriate vector to deliver nucleic acids and optimization of the conditions for insertion of the selected expression vector into the cell, are within the scope of one of ordinary skill in the art without the need for undue experimentation.

Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g., branched PEI)-DNA complexes; various nanoparticles and/or nanoshells such as multifunctional nanoparticles, metallic nanoparticles or shells (e.g., positively, negatively or neutral charged gold particles, cadmium selenide, etc.); ultrasound-mediated microbubble delivery systems; various dendrimers (e.g., polyphenylene and poly(amidoamine)-based dendrimers; etc.).

Viral vectors comprise a nucleotide sequence having sequences for the production of recombinant virus in a packaging cell. Exemplary viral vectors include but are not limited to: bacteriophages, various baculoviruses, retroviruses, and the like. Those of skill in the art are familiar with viral vectors that are used in "gene therapy" applications, which include but are not limited to: Herpes simplex virus vectors (Geller et al., Science, 241:1667-1669 (1988)); vaccinia virus vectors (Piccini et al., Meth. Enzymology, 153: 545-563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., Proc. Natl. Acad. Sci. USA, 85:6460-6464 (1988); Blaese et al., Science, 270:475-479 (1995); Onodera et al., J. Virol., 72:1769-1774 (1998)); adenovirus vectors (Berkner, Biotechniques, 6:616-626 (1988); Cotten et al., Proc. Natl. Acad. Sci. USA, 89:6094-6098 (1992); Graham et al., Meth. Mol. Biol., 7:109-127 (1991); Li et al., Human Gene Therapy, 4:403-409 (1993); Zabner et al., Nature Genetics, 6:75-83 (1994)); adeno-associated virus vectors (Goldman et al., Human Gene Therapy, 10:2261-2268 (1997); Greelish et al., Nature Med., 5:439-443 (1999); Wang et al., Proc. Natl. Acad. Sci. USA, 96:3906-3910 (1999); Snyder et al., Nature Med., 5:64-70 (1999); Herzog et al., Nature Med., 5:56-63 (1999)); retrovirus vectors (Donahue et al., Nature Med., 4:181-186 (1998); Shackleford et al., Proc. Natl. Acad. Sci. USA, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., Nature Genetics, 17:314-317 (1997), as well as viruses that are replication-competent conditional to a cancer cell such as oncolytic herpes virus NV 1066 and vaccinia virus GLV-1h68, as described in United States patent application 2009/0311664. In particular, adenoviral vectors may be used, e.g., targeted viral vectors such as those described in published United States patent application 2008/0213220.

Viral vectors expressing nucleic acid molecules of the present technology can be constructed based on viral backbones including, but not limited to, herpes simplex virus (HSV), vaccinia virus, cytomegalovirus, moloney murine leukemia virus, a retrovirus, lentivirus, adenovirus, adeno-associated virus, pox virus, or alphavirus (Warnock (2011) Methods in Molecular Biology 737:1-25). In some embodiments, the present technology provides a retroviral, e.g., a lentiviral, vector capable of delivering the nucleic acid molecules in vitro, ex vivo and/or in vivo. Any retrovirus or lentivirus belonging to the retrovirus family can be used for infecting both dividing and non-dividing cells with a nucleic acid molecule of the present technology, see e.g., Lewis et al (1992) EMBO J. 3053-3058.

In some embodiments, a retroviral or a lentiviral vector is a "minimal" lentiviral production system lacking one or more viral accessory (or auxiliary) gene. Exemplary lentiviral vectors can have enhanced safety profiles in that they are replication defective and self-inactivating (SIN) lentiviral vectors. Lentiviral vectors and production systems include e.g., those described in U.S. Pat. Nos. (USPNs) 6,277,633; 6,312,682; 6,312,683; 6,521,457; 6,669,936; 6,924,123; 7,056,699; and 7,198,784; any combination of these are exemplary vectors that can be employed in the practice of the present technology. In an alternative embodiment, non-integrating lentiviral vectors can be employed in the practice of the present technology. For example, non-integrating lentiviral vectors and production systems that can be employed in the practice of the present technology include those described in U.S. Pat. No. 6,808,923.

Viruses from retrovirus or lentivirus groups from "primate" and/or "non-primate" can be used; e.g., any primate lentivirus can be used, including the human immunodeficiency virus (HIV), the causative agent of human acquired immunodeficiency syndrome (AIDS), and the simian immunodeficiency virus (SIV); or a non-primate lentiviral group member, e.g., including "slow viruses" such as a visna/maedi virus (VMV), as well as the related caprine arthritis-encephalitis virus (CAEV), equine infectious anemia virus (EIAV) and/or a feline immunodeficiency virus (FIV) or a bovine immunodeficiency virus (BIV).

In alternative embodiments, retrovirus or lentiviral vectors are pseudotyped lentiviral vectors. In one aspect, pseudotyping includes incorporating at least a part of, or substituting a part of, or replacing all of, an env gene of a viral genome with a heterologous env gene, for example an env gene from another virus. In alternative embodiments, a lentiviral vector of the is pseudotyped with VSV-G. In an alternative embodiment, a lentiviral vector is pseudotyped with Rabies-G.

Retrovirus or lentiviral vectors may be codon optimized for enhanced safety purposes. Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms. Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev independent. Codon optimization also reduces homologous recombination between different constructs within the vector system (for example between the regions of overlap in the gag-pol and env open reading frames). The overall effect of codon optimization is therefore a notable increase in viral titer and improved safety. The strategy for codon optimized gag-pol sequences can be used in relation to any retrovirus.

Vectors, recombinant viruses, and other expression systems comprising nucleic acid molecules of the present technology can infect, transfect, transiently or permanently transduce a cell.

Also provided are host cells comprising a nucleic acid molecules or a vector disclosed herein, e.g., in vitro cells such as cultured cells, or bacterial or insect cells which are used to store, generate or manipulate the vectors, and the like. The nucleic acid molecules and vectors may be produced using recombinant technology or by synthetic means. A recombinant microorganism or cell culture can comprise an expression vector including both (or either) extra-chromosomal circular and/or linear nucleic acid (DNA or RNA) that has been incorporated into the host chromosome(s). In one aspect, where a vector is being maintained by a host cell, the vector may either be stably replicated by the cells during mitosis as an autonomous structure, or is incorporated within the host's genome.

In some embodiments, the host cells are primary patient cells, patient-derived xenograft models, cancer cell lines, stem cells, stable cell cultures, etc. Cancer cell lines are known in the art and can include, but are not limited to, OVCAR-3 cells, CAOV3, IGROV1, SK-OV-3, A2780, OVCAR-8 cells, PC9 cells, etc.

In specific embodiments, the cell may be a cancer cell.

In some embodiments, the invention provides a population of cells comprising a population of nucleic acid molecules as described herein, or a vector library as described herein. As described elsewhere herein, the cells may be cancer cells. The cells may be derived from cell lines or stable cell cultures.

Methods of Use

The present technology provides a barcoding scheme comprising transcribed barcodes. Unlike existing barcoding methods that enable the tracking of multiple cells solely at the DNA level, the barcoding scheme of the present technology comprising transcribed barcodes allows one to map the lineage to the transcriptional profile of a cell. Clonal and transcriptional analysis of a population of cells can be performed by employing a library that includes a plurality of nucleic acid molecules of the present technology, wherein each nucleic acid molecule comprises a molecular barcode having a variable sequence operably linked to a promoter. A population of target cells is contacted with a library under conditions sufficient for the nucleic acid molecules to enter into cellular members of the population of target cells, e.g., via transduction. The nucleic acid molecules and libraries thereof employed in methods of the present technology may vary greatly, where the type of library may be selected, at least in part, on the protocol to be employed to introduce the library members into the target cells. Aspects of the present technology include transducing a population of target cells with a vector library (e.g., a viral vector library) made up of a plurality of nucleic acid molecules of the present technology, wherein each nucleic acid molecule comprises a molecular barcode having a variable sequence operably linked to a promoter.

In one aspect, the present technology provides methods for tagging, uniquely identifying, or genetically barcoding a cell, a population of cells, or a culture of cells, comprising: (i) providing a cell, a population of cells or a culture of cells; (ii) providing at least one nucleic acid molecule according to the present technology, wherein the at least one nucleic acid is contained within a vector capable of stably transfecting, transducing, or infecting the cell; and (iii) transfecting, transducing, or infecting the cell, population of cells, or culture of cells with the vector, leading to the integration of an individual molecular barcode into the genomic DNA of the cell or each cell of the population or culture of cells, thereby tagging, uniquely identifying, or genetically barcoding the cell, population of cells, or culture of cells.

In one aspect, the present technology provides methods for simultaneously profiling the cell lineage and transcriptional state of single cells in a population of cells comprising: (i) stably transfecting, transducing, or infecting a population of cells with a vector library according to the present technology; (ii) allowing for transcription of the molecular barcode, the first reporter gene, and the second reporter gene; (iii) profiling the transcriptome of single cells in the population of cells by single cell sequencing; and (iv) associating the lineage of a single cell within the population with its transcriptional profile based on the expression of the molecular barcode. Methods for transfection, transduction, and infection are known in the art.

Methods of clonal analysis of functional genomic assays are provided. A functional genomic assay is performed according to any convenient protocol. Generally, a population of target cells is contacted with a barcode library in a manner sufficient for members of the library to be taken up by the target cells. For example, where the library is a viral vector library, the library may be contacted with the population of target cells under suitable transduction conditions. Transduction of the target cells with the viral vector library may be accomplished by any convenient protocol and may depend, at least in part, on the target cell type and the viral vectors employed. The transduction conditions may be optimized in order to achieve delivery and expression of a single unique clonal barcode construct into a given target cell. The target cells can be a pure, homogeneous population of the same or similar cells or the target cells can be a heterogeneous population of different cell types. The target cells may be cultured, or may be tissues, organs, biological fluids or whole organisms, where the organism is (in some instances) a human, mouse or rat. The library may be co-transduced with a reporter vector in order to extend selection of target cells to a variety of in vivo and in vitro biological assays.

The number of target cells that are contacted and transduced with the barcode library may be selected so as to provide for sufficient clonal analysis, such that the number may be chosen in view of the complexity of the library. Once a founder population in which almost every cell has a different molecular barcode and associated unique transcript is established, the transduced cells may be expanded to generate clonal populations, where each clonal population has its own barcode. Nucleic acids may be isolated and sequenced.

Once transduced, the target cells can be assayed for a particular characteristic (e.g., phenotype) of interest. Assay protocols may be pooled or array formats, as desired.

Selection strategies of such assays may vary, as desired, where the particular selection strategy employed depends, at least in part, on the characteristic of interest. The characteristic of interest may vary greatly, ranging from growth rate to the appearance of a particular phenotype of interest, such as the expression of a reporter construct, specific marker, etc. In some embodiments, high throughput protocols may be employed. In some embodiments, the assay may include a step of exposing the cells to a stimulus, e.g., exposure to an active agent, drug, a physical stimulus, and electromagnetic radiation stimulus, stress, etc. The transduced cells could be analyzed for specific phenotype or isolated (selected) based on specific phenotype.

The cells may be further analyzed to identify both the clonal barcode and transcriptional profile of the cell to identify any gene signatures at least putatively giving rise to the characteristic of interest. The clonal barcode and transcriptional profile may be identified using any convenient protocol. Protocols of interest include, but are not limited to: sequencing protocols, e.g., high throughput sequencing protocols, and hybridization protocols, e.g., array based hybridization protocols. A given protocol may include various steps well-known to those of skill in the art, including but not limited to: nucleic acid amplification, separation, hybridization, labeling, label detection, sequencing, etc. In some embodiments, the methods include a high throughput selection and clonal barcode identification protocol. In certain embodiments, these embodiments exploit the advantages of high-throughput (HT) sequencing platforms to rapidly identify enriched inserts, for example, in FACS-selected cell fractions wherein particular members of the population are identified by activation of a detectable reporter gene.

Once the clonal barcode and transcriptional profile are mapped, the resultant data may be employed in clonal analysis of the genomic assay. Because each different transducing nucleic acid molecule is barcoded and the barcode is identified, the number of different clonal populations (and therefore individual precursor target cells actually transduced with a member of the barcode library) may be readily determined. This information may then be used for a variety of different purposes.

The methods of clonal analysis, e.g., as described herein, may be employed in a variety of different genomic assays for a variety of different purposes. Examples of applications in which clonal analysis may be employed include, but are not limited to: determination of mechanisms and/or gene signatures underlying response to drug treatment, non-inherited drug resistance, tumor dormancy, migration and metastatic seeding, response to EMT, response to stress, response to nutrient deprivation, response to hypoxia, identification of stem-cell like markers, identification of markers determining length of lag phase and likelihood of relapse after drug treatment, etc. (e.g., in cancer cells, cancer cell lines, tumor models, PDX tumor models, etc.).

For genomic assays, a founder population established as described above, can be propagated and separated into approximately identical replicate groups, and subjected to various treatments depending on the biological pathway being examined.

In some embodiments, the nucleic acids of the present technology are useful for studying recurrence of disease in relapse models (e.g., a HGSOC relapse model to study for e.g., platinum-sensitive relapse). The nucleic acids may comprise (i) a molecular barcode having a variable sequence operably linked to a promoter, (ii) a polynucleotide comprising a first reporter gene operably linked to a constitutive promoter, and (iii) a polynucleotide comprising a second reporter gene operably linked to an inducible promoter system, wherein the detection of the gene product of the second reporter gene is indicative of the proliferative status of the cell. Methods such as flow cytometry and imaging can be employed to characterize and quantify lag phase distribution (time-to-relapse), and the contribution of dormancy to relapse. The methods can also include profiling the transcriptome of barcoded cells at different time points throughout treatment: prior to treatment, post-treatment, and following relapse and gene signatures can be derived from each time point.

In some embodiments, the present technology provides a method of identifying genes associated with tumor dormancy comprising: (i) stably transfecting, transducing, or infecting a population of cells with a vector library according to the present technology, wherein the detection of the gene product of the second reporter gene is indicative of the proliferative status of the cell; (ii) propagating and dividing the cells into identical control and treatment replicate groups; (iii) profiling the transcriptome and lineage of single cells in the control replicate group; (iv) treating the treatment replicate group with a cancer therapeutic; (v) profiling the transcriptome and lineage of single cells in treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v), and (vi) to identify genes associated with tumor dormancy. Any molecule (e.g., protein) that is partitioned equally between sister cells during cell division can serve as a reporter of the proliferative status of the cell. Such reporter molecules are known in the art.

In some embodiments, the method may further comprise measuring the dilution of gene product of the second reporter over time, wherein the dilution is indicative of proliferative history.

In some embodiments, the present technology provides a method of identifying genes associated with stem-cell like treatment-resistant cancer cells comprising: (i) stably transfecting, transducing, or infecting a population of cells with a vector library according to the present technology, wherein the detection of the gene product of the second reporter gene is indicative of the proliferative status of the cell; (ii) propagating and dividing the cells into identical control and treatment replicate groups; (iii) profiling the transcriptome and lineage of single cells in the control replicate group; (iv) treating the treatment replicate group with a cancer therapeutic; (v) profiling the transcriptome and lineage of single cells in treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v), and (vi) to identify genes associated with stem-cell like treatment-resistance cancer cells. Any molecule (e.g., protein) that is partitioned equally between sister cells during cell division can serve as a reporter of the proliferative status of the cell. Such reporter molecules are known in the art.

In some embodiments, the present technology provides a method of identifying genes associated with response to a cancer therapeutic comprising: (i) stably transfecting, transducing, or infecting a population of cells with a vector library according to the present technology, wherein the detection of the gene product of the second reporter gene is indicative of the proliferative status of the cell; (ii) propagating and dividing the cells into identical control and treatment replicate groups; (iii) profiling the transcriptome and lineage of single cells in the control replicate group; (iv) treating the treatment replicate group with a cancer therapeutic; (v) profiling the transcriptome and lineage of single cells in treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v), and (vi) to identify genes associated with response to the cancer therapeutic. Any molecule (e.g., protein) that is partitioned equally between sister cells during cell division can serve as a reporter of the proliferative status of the cell. Such reporter molecules are known in the art.

In some embodiments, the present technology provides a method of identifying genes associated with migration and metastatic seeding comprising: (i) stably transfecting, transducing, or infecting a population of cells with a vector library according to the present technology, wherein the detection of the gene product of the second reporter gene is indicative of the proliferative status of the cell; (ii) propagating and dividing the cells into identical control and treatment replicate groups; (iii) profiling the transcriptome and lineage of single cells in the control replicate group; (iv) treating the treatment replicate group with a cancer therapeutic; (v) profiling the transcriptome and lineage of single cells in treatment replicate group in the lag phase following the treatment; (vi) profiling the transcriptome and lineage of single cells in the treatment replicate group following relapse; (vii) deriving gene signatures from (iii), (v) and (vi); and (viii) comparing the gene signatures derived from (iii), (v), and (vi) to identify genes associated with migration and metastatic seeding. Any molecule (e.g., protein) that is partitioned equally between sister cells during cell division can serve as a reporter of the proliferative status of the cell. Such reporter molecules are known in the art.

The gene signatures derived using methods of the present technology may be used to generate a set of candidate genes/pathways predicted to contribute to the pathway being studied. The predictions may be validated using known experimental techniques in appropriate models.

In some embodiments, next-generation sequencing or NGS methods are employed. NGS refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than 103, 104, 105 or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. Nature Biotechnology Reviews 11:31-46 (2010). In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, solid sequencing, Ion semiconductor sequencing, Helioscope single molecule sequencing etc.

Articles of Manufacture and Kits

The present technology provides kits comprising the nucleic acid molecules of the present technology. In certain embodiments, the kit comprises a vector library comprising the nucleic acid molecules of the present technology. In some embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the nucleic acid molecules or vector libraries can be provided together with instructions for delivering the nucleic acid molecules to a target cell population. The instructions may be printed directly on the container (when present), or as a label applied to the container, or as a separate sheet, pamphlet, card, or folder supplied in or with the container.

EXAMPLES

Example 1: Establishment of an In Vitro Platinum-Sensitive Recurrence Model

Figure 1B:
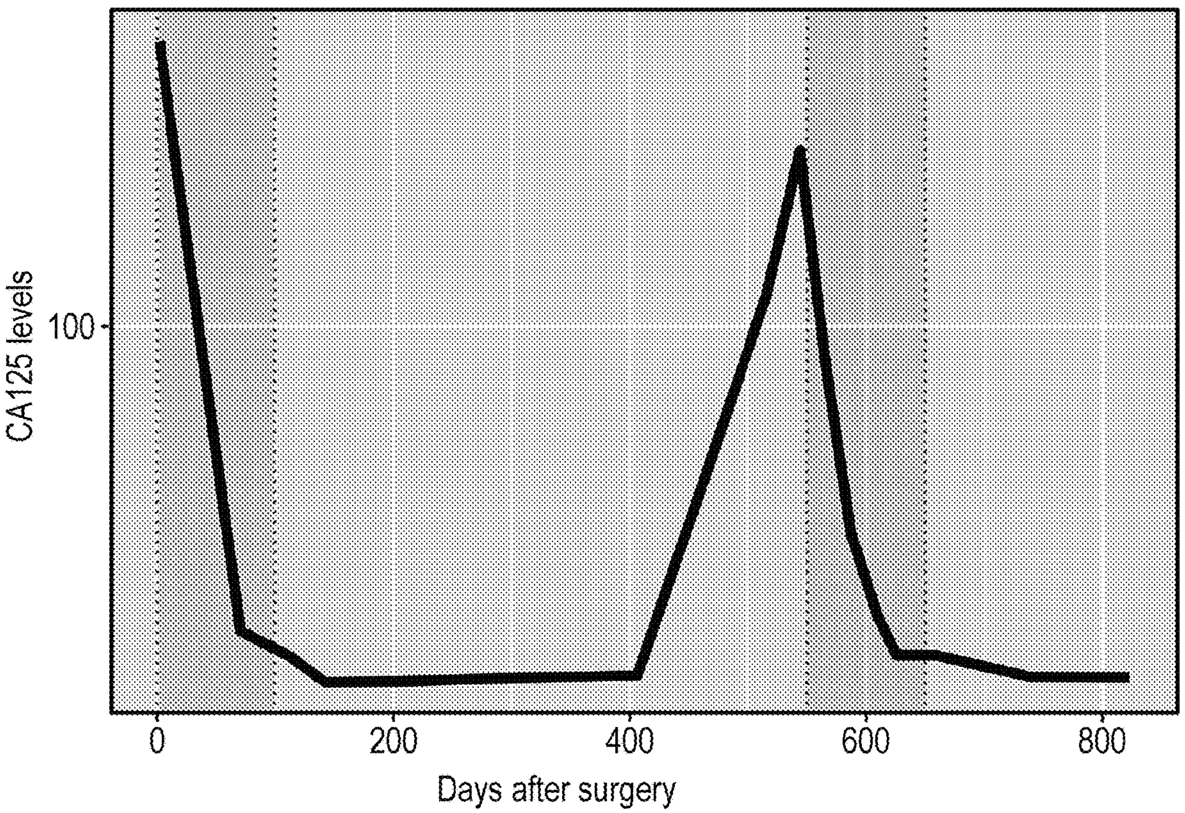
Figure 1C:
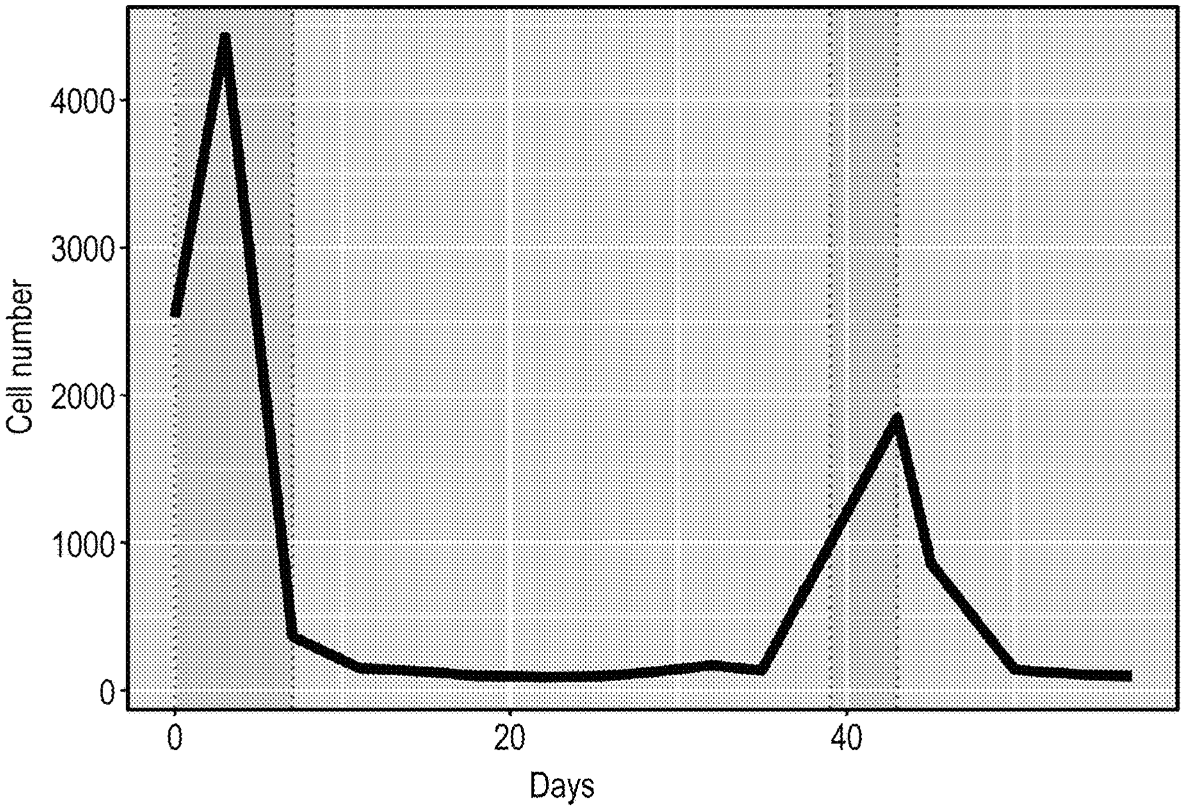
Figure 1D:
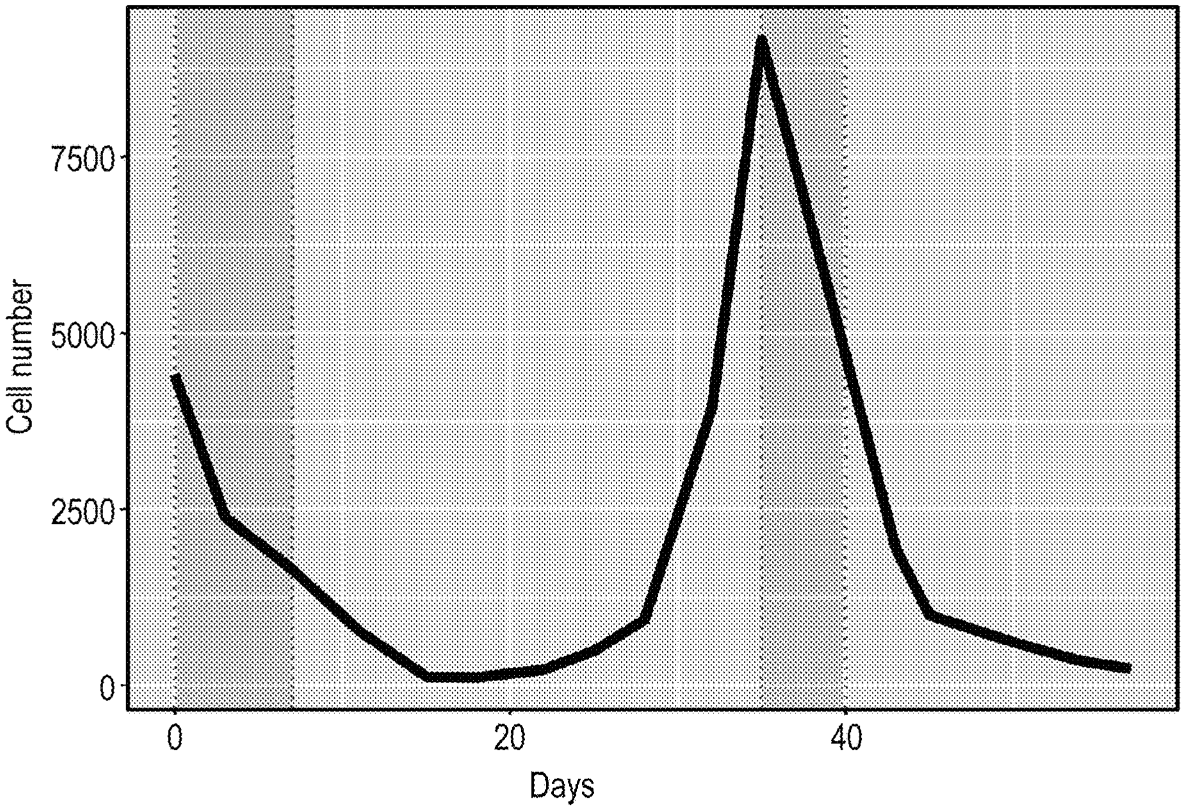
Figure 1E:
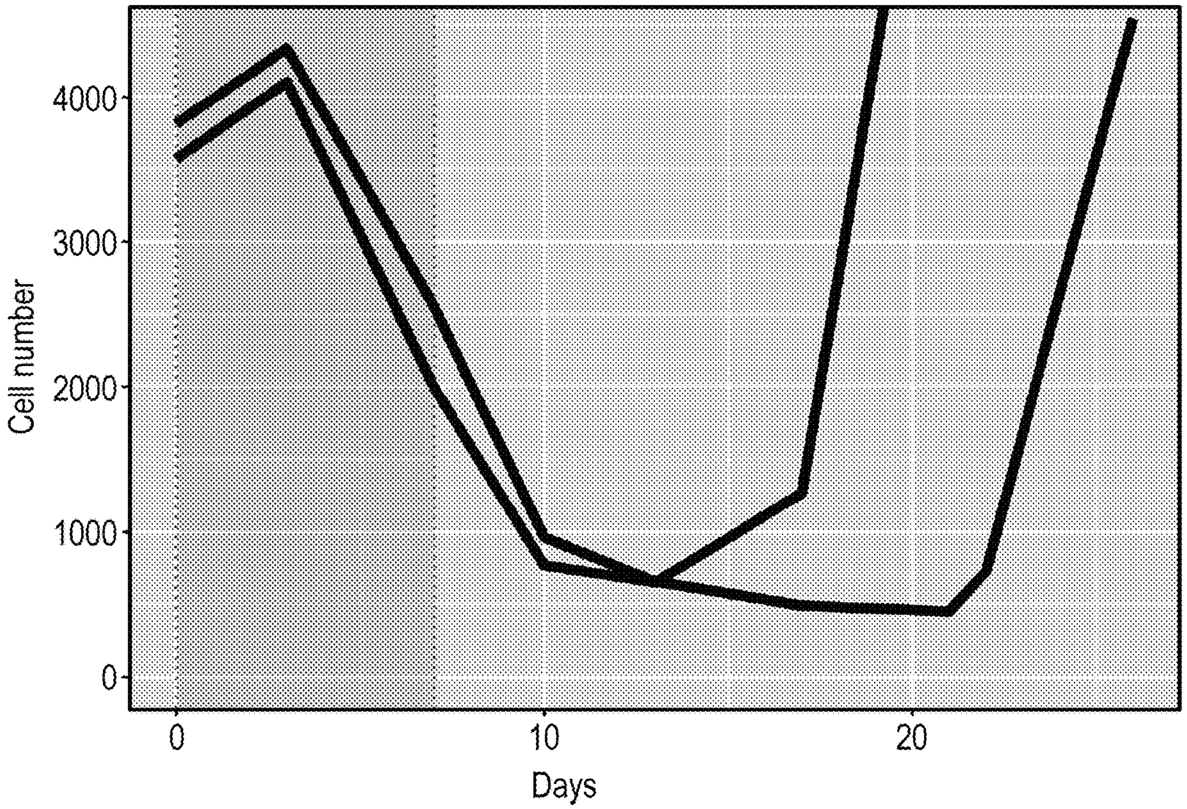

While much effort has been focused on experimental models to study the emergence of platinum-resistance (Cunnea & Stronach, Front Oncol 4:81 (2014)), little attention has been given to the development of robust methods to model platinum-sensitive relapse. As the clinical classification of relapse is based both on the effectiveness of the treatment and the time to recurrence, the present study aimed to establish a system that can capture both these aspects. Analogous to the CA125 levels that are used to monitor disease progression in patients, direct measurement of cell number was used to monitor response in vitro. To this end, an OVCAR3 H2B-GFP cell line was generated. OVCAR3 is a commonly used HGSOC model and the H2B-GFP allows the easy quantification of the number of live cells during the course of drug treatment. It was found that following six days of treatment with either carboplatin or cisplatin, the majority of cells died and the remaining cells entered a non-dividing lag phase (FIG. 1A). While most surviving cells remained arrested throughout the course of the experiment, a small subpopulation divides and repopulated the dish. This 'persisters' population is not platinum-resistant and responds to a second round of treatment. This response was quantified based on time-lapse images and a striking similarity was found between the pattern of platinum-sensitive relapse observed in patients (FIG. 1B), as measured by CA125 levels, and the pattern observed in vitro in this study (FIG. 1C-D). FIG. 1B shows platinum-sensitive relapse in a patient (CA125 data obtained from Bowtell et al., Nat Rev Cancer 15:668-79 (2015)). FIG. 1C shows in vitro carboplatin-sensitive relapse (6.25 μM treatment) in the OVCAR3 H2B-GFP model. FIG. 1D shows in vitro cisplatin-sensitive relapse (50 μM treatment) in the OVCAR3 H2B-GFP model. Interestingly, despite similar initial response, well-to-well variability was observed in time-to-relapse (FIG. 1E), which is in line with the dramatic differences in time-to-relapse observed in patients with a similar initial response to treatment. In all the cases observed, the OVCAR3 H2B-GFP population that emerged after the first drug treatment was platinum sensitive, thus recapitulating the reversible resistance seen in the clinic.

Example 2: Generation of the Watermelon Library

To facilitate the ability to distinguish the relative contribution of tumor dormancy, stochastic cell state shifts and stem cell-like populations to platinum-sensitive relapse, the Watermelon lentiviral barcode library was developed (FIG. 2). This library has three unique features:

I. Lineage Tracing at the Transcriptome Level.

Figure 4A:
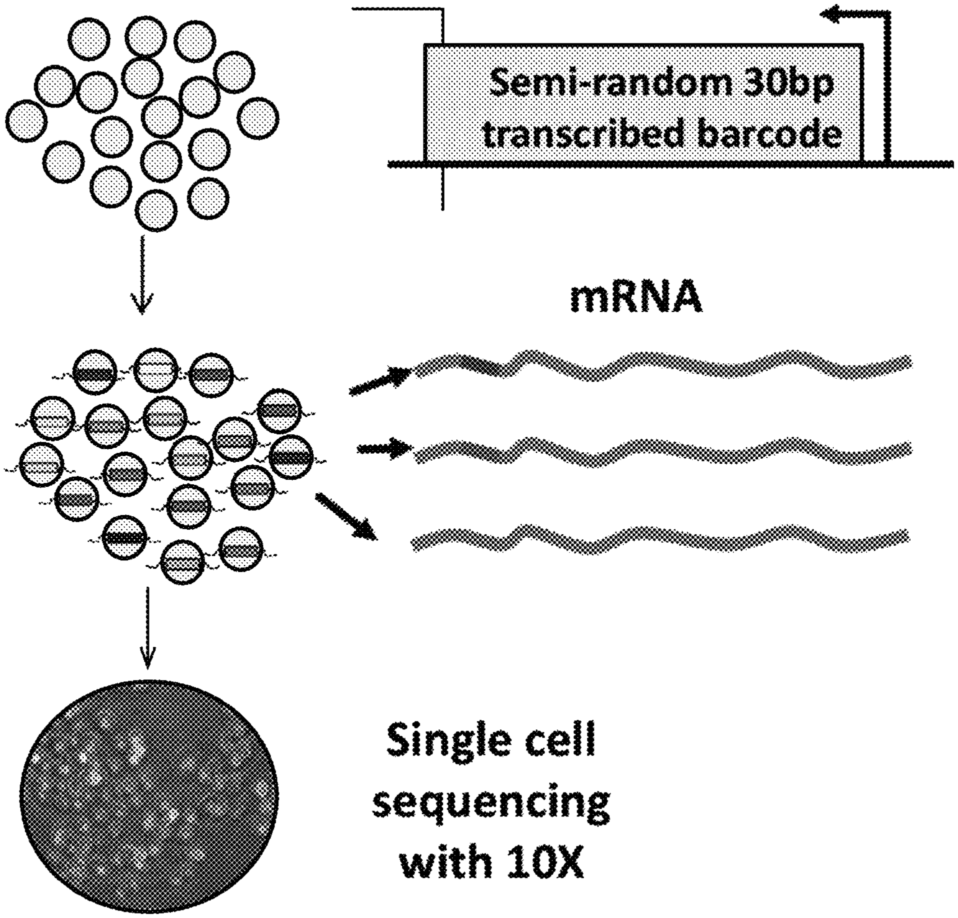
FIGS. 4A-4C show lineage tracing at the single cell level in Watermelon-transduced cells.

Existing DNA barcoding methods, such as ClonTracer (Bhang et al. Nat Med 21:440-8 (2015)), have proven to be a powerful tool for studying genetic drug resistance. The basic concept behind DNA barcoding involves the use of a lentiviral vector which carries a unique DNA sequence as a lineage marker. Because all the progeny of a given lentivirus-transduced cell are expected to harbor the same sequence, changes in the frequency of lineage-associated sequences (i.e. barcodes) in response to therapy can be used to study the mechanisms underlying resistance. For instance, ClonTracer was used to demonstrate that most EGFR inhibitor-resistant clones in a non-small cell lung cancer cell line were pre-existing and selected for during treatment (Bhang et al.). However, because this system requires cell lysis in order to amplify the DNA barcodes, the transcriptional profile of the cells cannot be recovered. To facilitate the simultaneous tracing of cell lineage and transcriptional state, which is imperative for studying non-genetic resistance, a library in which the barcode is expressed in a manner that can be captured using SC sequencing was generated (FIG. 4A). Because each clonal population derived from a Watermelon-transduced cell line expresses a unique barcode transcript, the contribution of lineage and transcriptional state to drug sensitivity can be de-convoluted.

II. Proliferation Tracking.

Figure 3A:
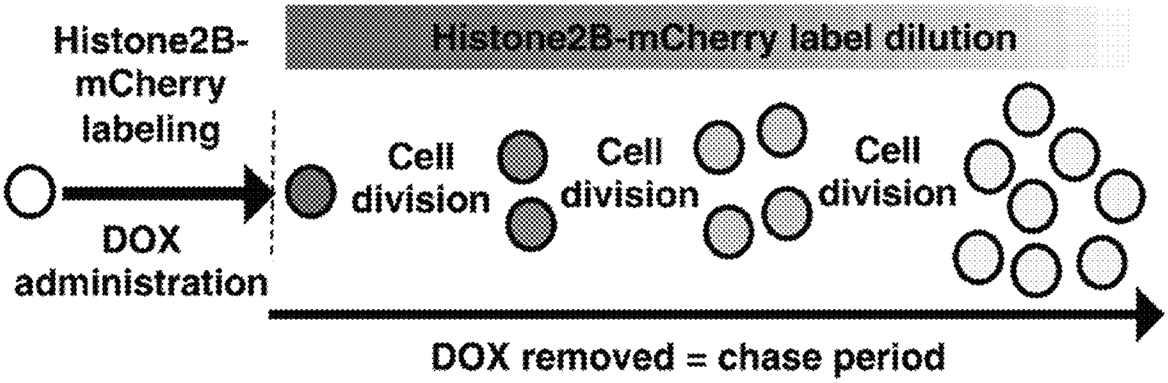
FIGS. 3A-3D show the function of H2B-mCherry as a reporter of proliferative history.

Watermelon includes a doxycycline(dox)-inducible H2B-mCherry-labeling scheme to monitor each cell's proliferative state. Following a pulse of induction, H2B-mCherry partitions between daughter cells, such that H2B fluorescence intensity correlates with the number of divisions a cell has undergone since labeling (FIG. 3A). Notably, H2B histone protein will incorporate into chromatin in a replication-independent manner thus allowing the labeling of non-dividing cells. Because H2B-mCherry transcription is turned off once the inducer is washed away, only quiescent or very slow proliferating cells are expected to remain red long after dox chase. Unlike dye label retention methods, H2B retention genetic systems do not diffuse into the surrounding area, rendering them especially suitable for long-term assays. Indeed, H2B labeled cells can be detected in vivo months after induction (Sawen et al. Cell Rep 14:2809-18 (2016)). This proliferation tracking system allows the assessment of the contribution of slow cycling cells to disease recurrence.

III. High Throughput Live Cell Imaging.

Cells transduced with Watermelon constitutively express a nuclear green fluorophore reporter (NLS-mNeon) and express an additional red nuclear reporter (H2B-mCherry) upon exposure to dox. This allows monitoring and systematic evaluation of live cell drug response at the population- and SC-level in vitro.

Figure 3B:
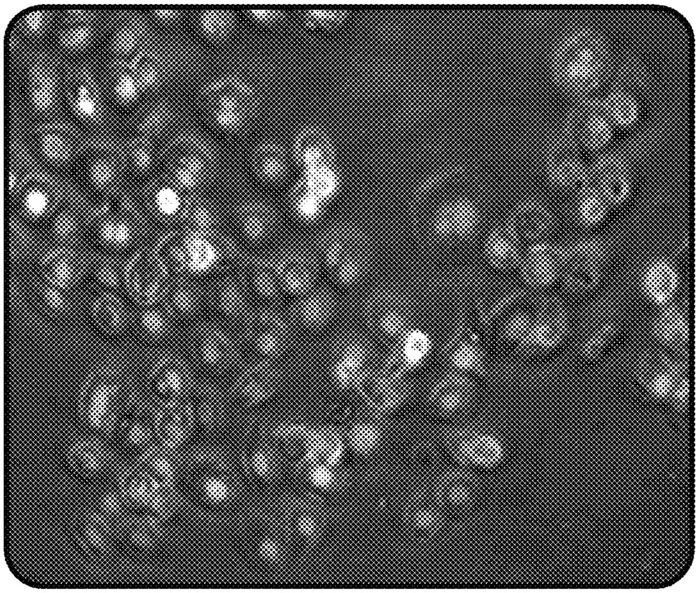
Figure 3C:
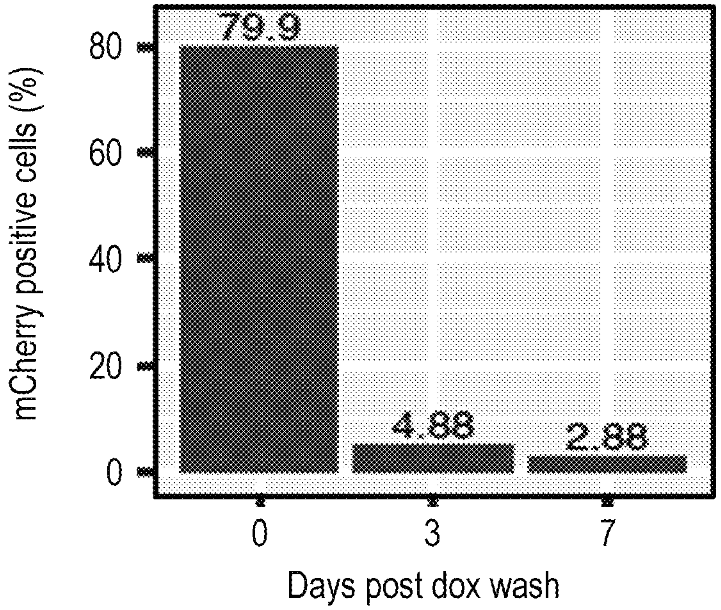
Figure 3D:
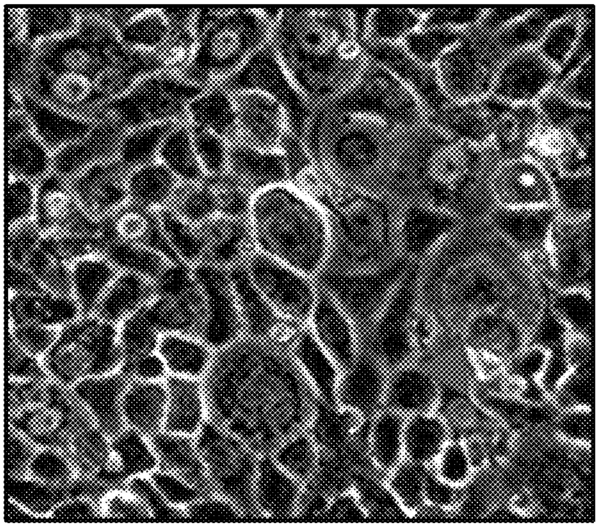

Deep sequencing confirmed that the generated Watermelon library contains more than a million barcodes with an overall balanced GC content. Watermelon-transduced cells grown in dox-containing media express both a green and a red nuclear fluorophore making them easily traceable with a standard fluorescent microscope (FIG. 3B). Fluorescence dilution of H2B-mCherry over time serves as a reporter of proliferative history. Using flow cytometry, the fluorescence dilution of H2B-mCherry was confirmed by monitoring the reduction of mCherry-positive cells over time (FIG. 3C). Cells transduced with the Watermelon library were exposed to dox for 48 hours prior to starting the experiment and mCherry-positive cells were monitored over time. The percentages of red cells at the time of measurement is indicated above each bar. In line with the flow cytometry data, imaging revealed a small number of red dormant cells even two weeks after dox chase (FIG. 3D).

Figure 4B:
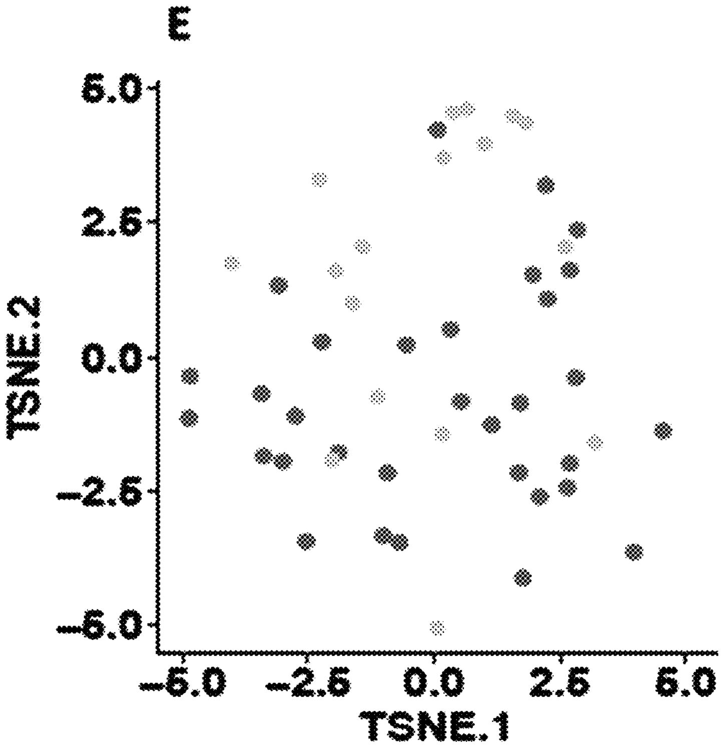
Figure 4C:
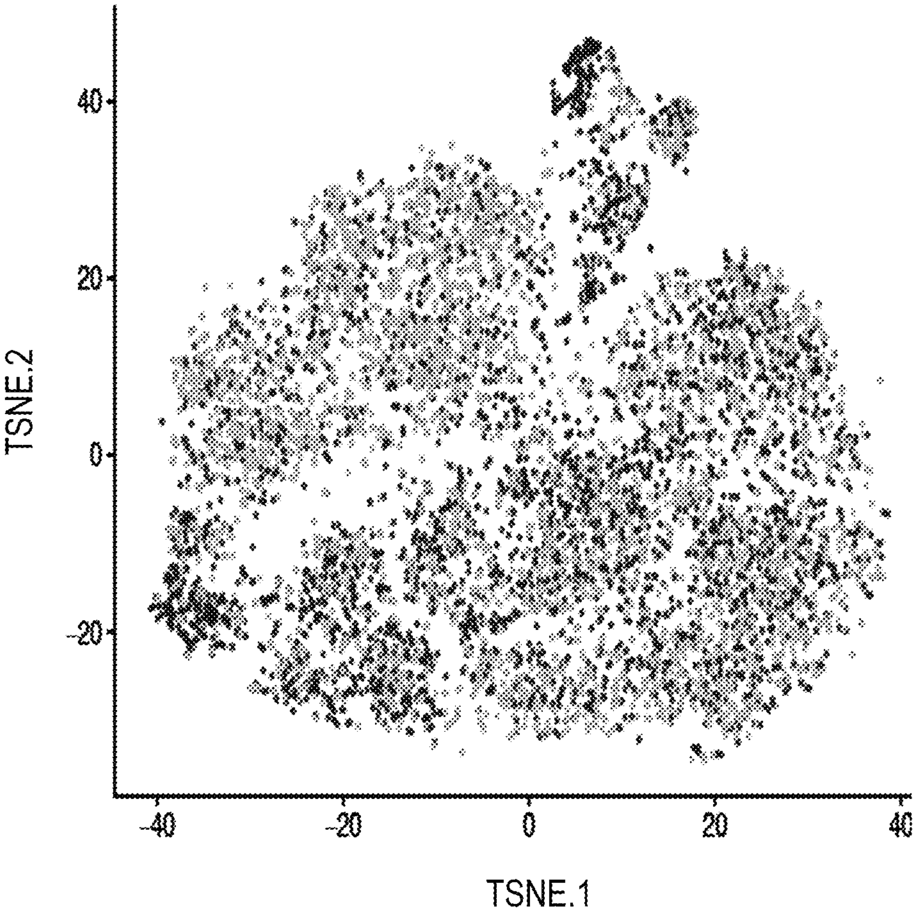

Additionally, the lineage of cells was successfully mapped using SC RNA-Seq. FIG. 4B shows the t-distributed stochastic neighbor embedding (tSNE) analysis of 49 cells transduced with the Watermelon library in a pilot experiment. The lineage of 65% of examined cells was successfully mapped and cells where lineage information was successfully obtained from single cell data are marked in red. In a further study, 9,355 cells transduced with the Watermelon library were examined. FIG. 4C shows the tSNE analysis of these cells. Cells where lineage information was successfully obtained from single cell data are marked in red.

More broadly, this work can be generalized to studying non-genetic resistance mechanisms in other cancers and underscores the power of simultaneously tracing the lineage as well as the transcriptional and proliferative state of each cell in a population of cells.

Example 3. Generation of SCRNA-Seq Profiles of OC Clinical Samples

Figure 5:
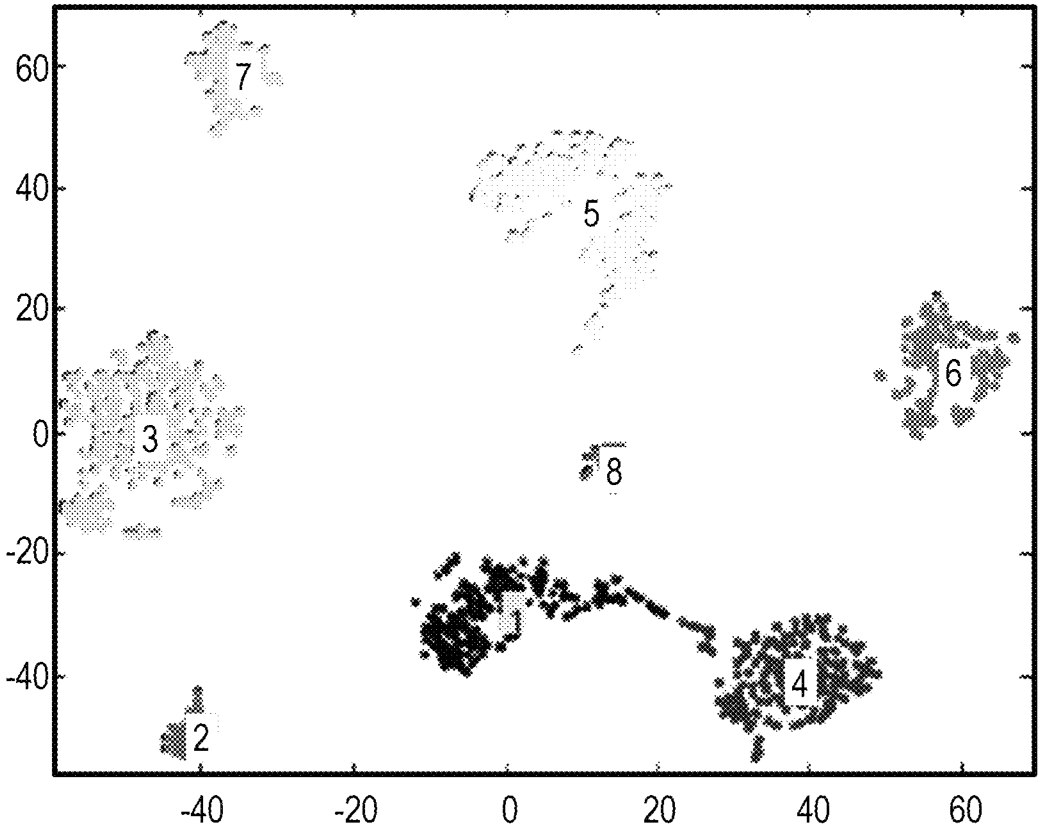
FIG. 5 shows a tSNE plot grouping malignant ascites cells into clusters based on similar expression profiles. 1297 single cells from six patient samples were profiled by plate-based single-cell RNA-seq and clustered according to their transcriptomes. Differential expression across these clusters indicated that the vast majority of ascites cells clustered primarily by their patient of origin.

Cancer cells were isolated from peritoneal tumor fluid based on expression of EPCAM and CD24, surface markers previously shown to be specific to OC cells (Peterson et al. Proc Natl Acad Sci USA 110:E4978-86 (2013)) to characterize the ecosystem of HGSOC ascites collected from patients. In total, 1297 cells from six individuals were sorted and profiled using a modified Smart-Seq2 protocol. 1297 single cells from six patient samples were profiled by plate-based single-cell RNA-seq and clustered according to their transcriptomes. Differential expression across these clusters indicated that the vast majority of ascites cells clustered primarily by their patient of origin (FIG. 5). Additional pairs of treatment-naïve and relapse samples are sequenced to extend this dataset. The gene signatures derived from the experimental relapse model are compared to those derived from SC patient data to generate a list of clinically-relevant relapse-associated pathways.

Example 4. Characterization of Watermelon-Transduced Platinum-Sensitive Relapse Models Characterization of Lag Phase Following Drug Treatment.

The disease course leading to platinum-sensitive relapse can be divided into three phases: primary disease, lag phase and recurrence2. Following first-line therapy, patients typically enter a "lag phase" marked by the absence of any active disease, with serum CA125 levels comparable to those of healthy women. The OVCAR3 experimental system described in Example 1 recapitulates this distinct phase following platinum treatment before a small population of cells resumes growth.

Notably, like in patients, variability exists not only in overall initial chemosensitivity of cancer cells but also in time-to-relapse of drug tolerant cells. To characterize lag phase distribution, multiple 384-well plates are screened to profile hundreds of relapse events and the time-to-relapse as well as the percentage of arrested and proliferative chemoresistant cells are calculated. These data are used to calculate relapse distribution of unperturbed cells that would be used as a baseline by which to assess the effects of any perturbations. In addition, to test if arrested lag phase cells undergo changes, the cell cycle, DNA damage, and transcriptome of cells is measured in early, middle and late lag phase. Time points for this experiment are chosen based on the distribution obtained from the relapse characterization screen described herein. This workflow results in a better understanding of the factors that determine treatment free intervals in recurrent ovarian cancer.

Measurement of the Contribution of Dormant Cells to Platinum-Sensitive Relapse.

The contribution of dormant cells to platinum-sensitive relapse is measured by monitoring slow proliferating cells. Specifically, by repeating the drug treatment course with a cell population that contains only a small fraction of label-retaining red cells, the contribution of dormancy to overall cell survival and to the ability to resume proliferation is measured by imaging. In addition, mathematical modeling and simulations are used to measure what fraction of the observed relapse distribution can be attributed to 'awakening' dormant cells. Without wishing to be bound by theory, this elucidates the role of slow cycling cells in OC chemoresistance and relapse.

Establishment of an Analogous In Vivo Relapse Model.

To study platinum-sensitive relapse in a physiologically relevant context, established HGSOC PDX models (Liu, J. F. et al. Clin Cancer Res 23:1263-73 (2017)) are transduced with the Watermelon library and in vivo relapse patterns are characterized following a second drug treatment.

Example 5. Profiling the Transcriptome of Cells Throughout Treatment and Relapse Monitoring the Relation of Changes in Cell State to a Cell's Lineage.

The transcriptome of Watermelon-transduced cells is profiled in each of these three phases: treatment-naïve, lag phase following treatment, and relapse. Signatures associated with stemness and epithelial-mesenchymal transition to cell lineage are mapped and how they change throughout the course of treatment and relapse is studied. Without wishing to be bound by theory, this shows that OC stem cells are the source of disease recurrence and uncovers the role that additional transient cell states in relapse.

Expansion of Patient SC Data Set and Extraction of Relapse Signature.

SC profiles of matched treatment-naïve and relapse samples of HGSOC patients are generated using the protocol developed by Dr. Izar.

Generation of a List of Clinically-Relevant Gene Signatures.

The patient-derived data is used to refine a set of clinically-relevant signatures that can be further studied in in vivo and in vitro experimental systems described herein. This iterative process overcomes the inherent challenge of identifying meaningful pathways solely based on a small number of patient samples and avoids the pitfalls associated with working solely with ex vivo cancer models. The identification of relapse-associated genes provides the stepping-stone for the development of targeted treatments.

Example 6. Targeting Clinically-Relevant Pathways Involved in Relapse

The Signatures Predict Disease Outcome.

The transcriptome-derived signatures are used to predict disease-free interval and overall survival rate in order to facilitate the identification of those patients most likely to have a favorable response to therapy.

Perturbation of Pathways Involved in Relapse.

The contribution of the top scoring candidates to relapse is measured using different experimental approaches: knock-outs (with CRISPR/Cas9 and related approaches), knockdown (with CRISPRi) and pharmacological inhibitors. In each case, the perturbation's effect on the number of surviving chemoresistant cells as well as the time-to-relapse is measured. As a complementary approach, gain-of-function by manipulating cells to express signatures that are associated with a large percentage of surviving cells or a shorter lag phase, two phenomena that are associated with advanced treatment-refractory disease, is studied. This systematic screen will uncover new targets whose inhibition could potentially extend treatment-free intervals and overall patient survival.

Example 7. Modeling Non-Inherited Drug Resistance of PC-9 Cells to EGFR Tyrosine Kinase Inhibitors (TKIs)

Figure 6A:
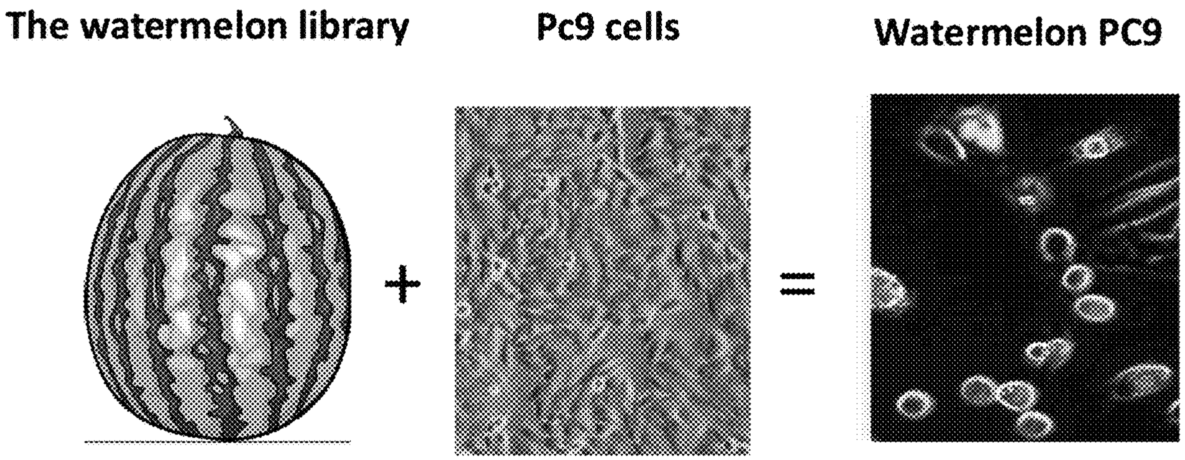
FIGS. 6A-6D show the modeling of non-inherited drug resistance of PC-9 cells to EGFR tyrosine kinase inhibitors (EGFR-TKI).
Figure 6B:
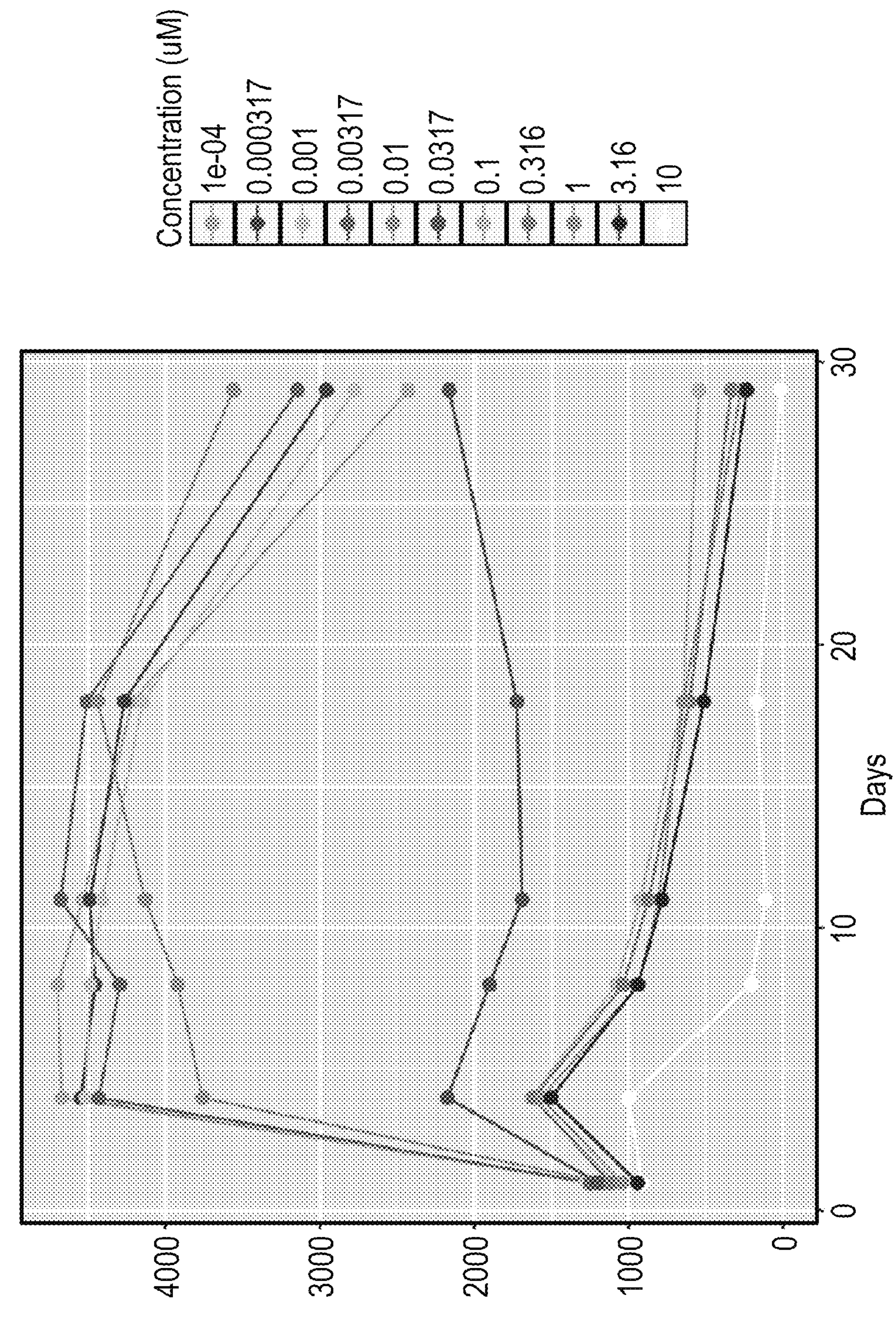
Figure 6C:
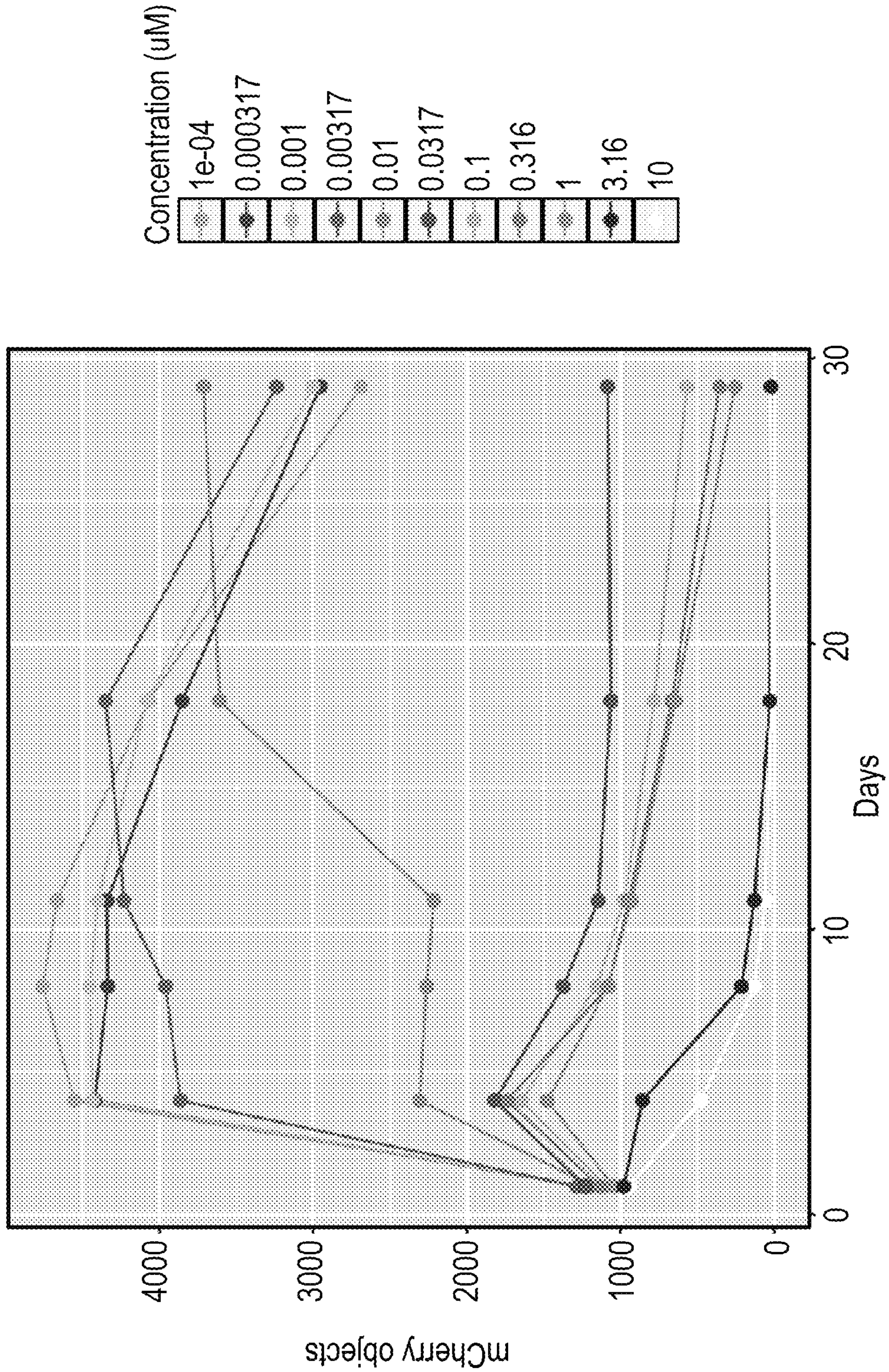
Figure 6D:
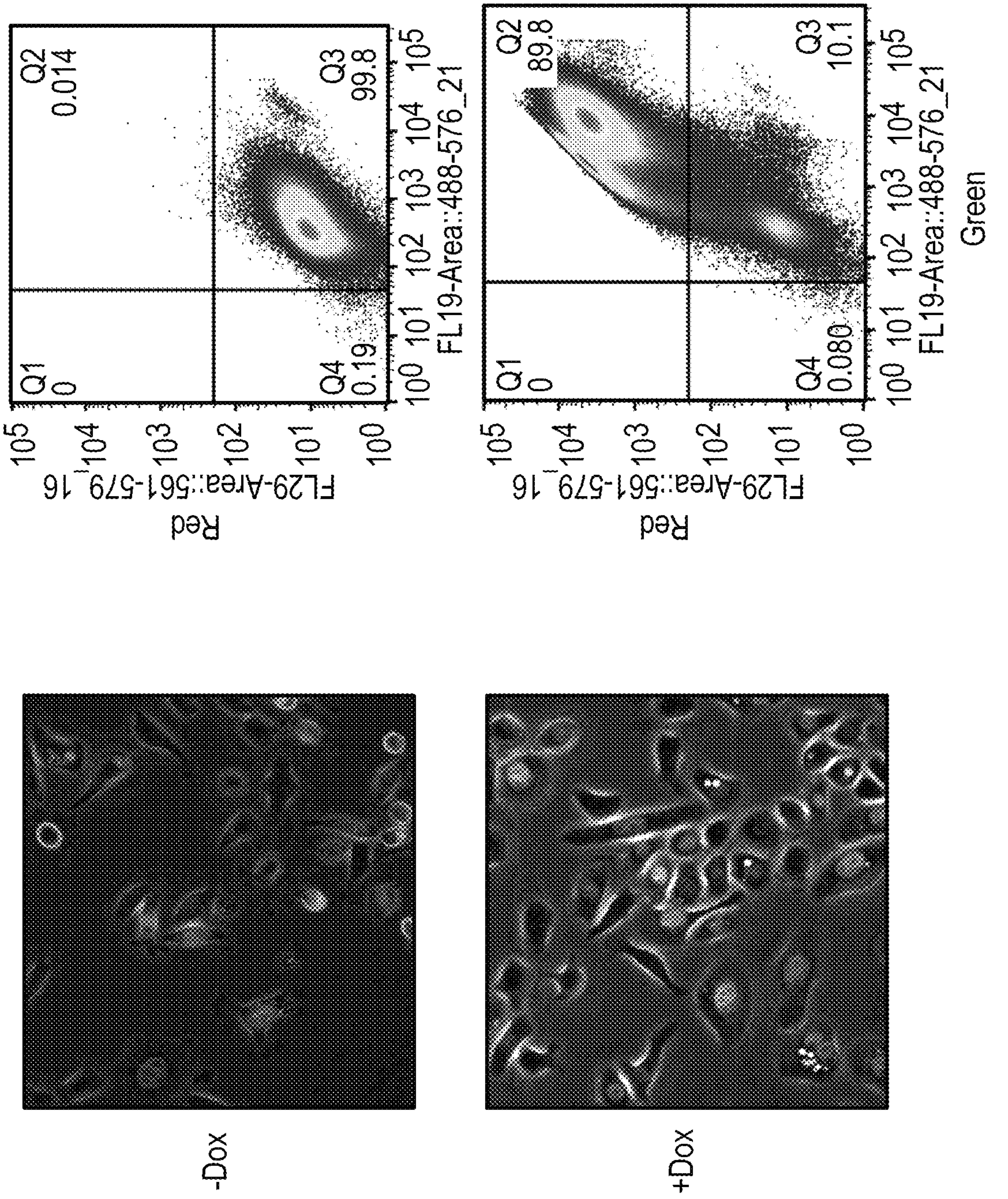

To demonstrate the modeling of non-inherited drug resistance of PC-9 cells to EGFR-TKIs, PC-9 cells were transduced with the Watermelon library (FIG. 6A). The Watermelon-transduced PC-9 cells were sensitive to the EGFR-TKIs, gefitinib and osimertinib (FIGS. 6B and 6C), and were responsive to dox-induction (FIG. 6D).

Figure 7A:
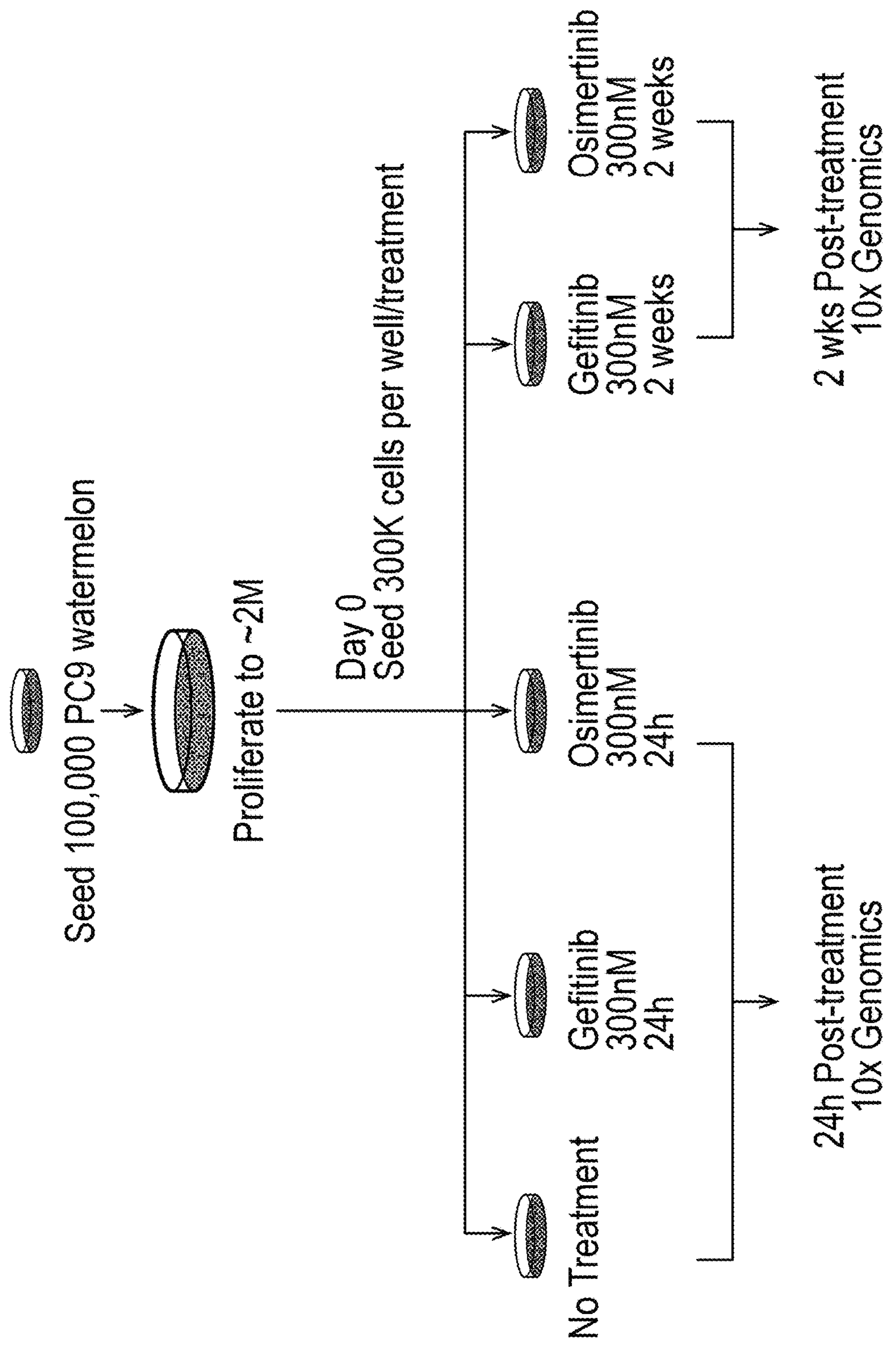
FIGS. 7A-7C show the lineage and transcriptome analysis of Watermelon-transduced PC-9 cells.
Figure 7B:
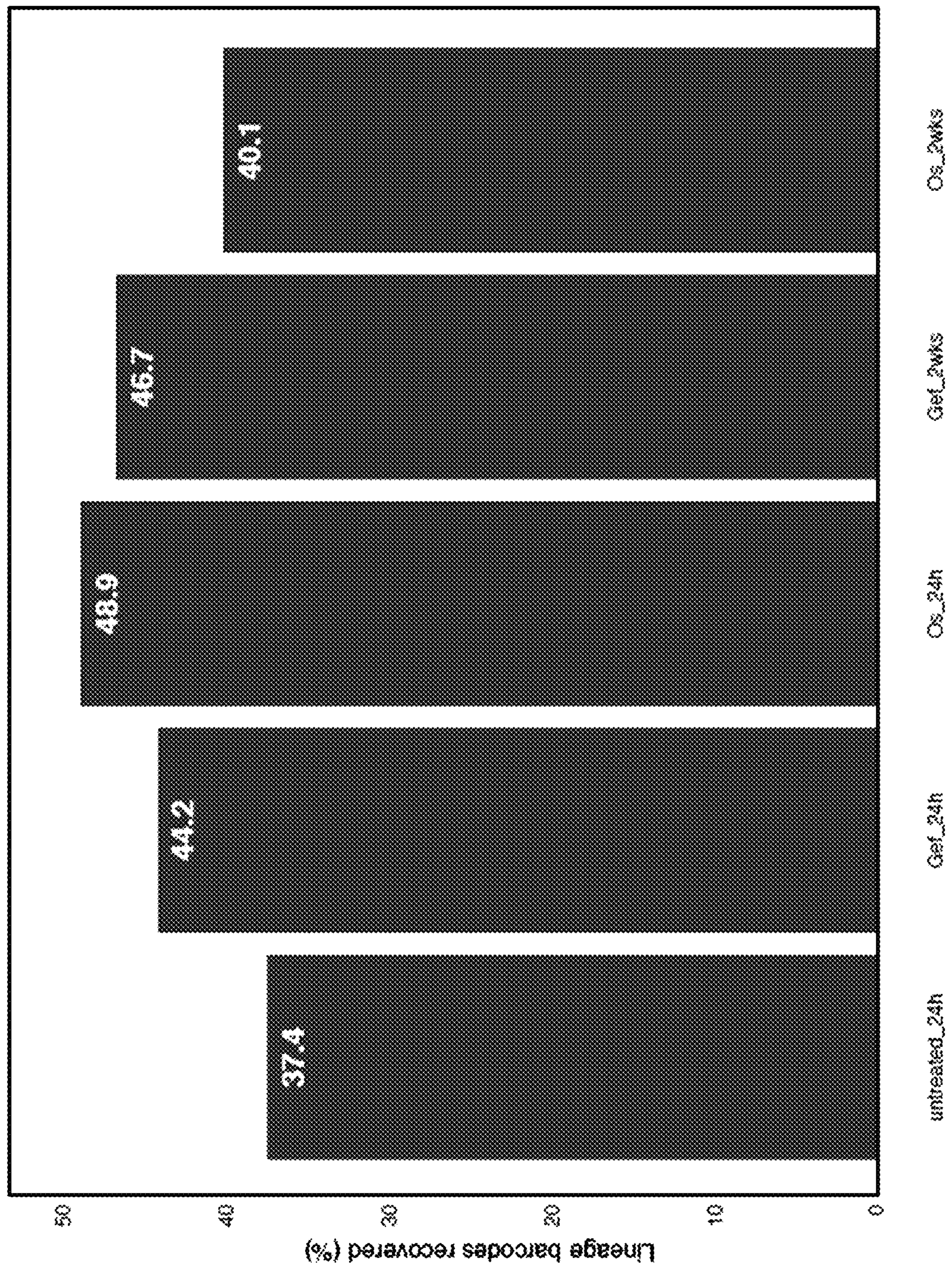
Figure 7C:
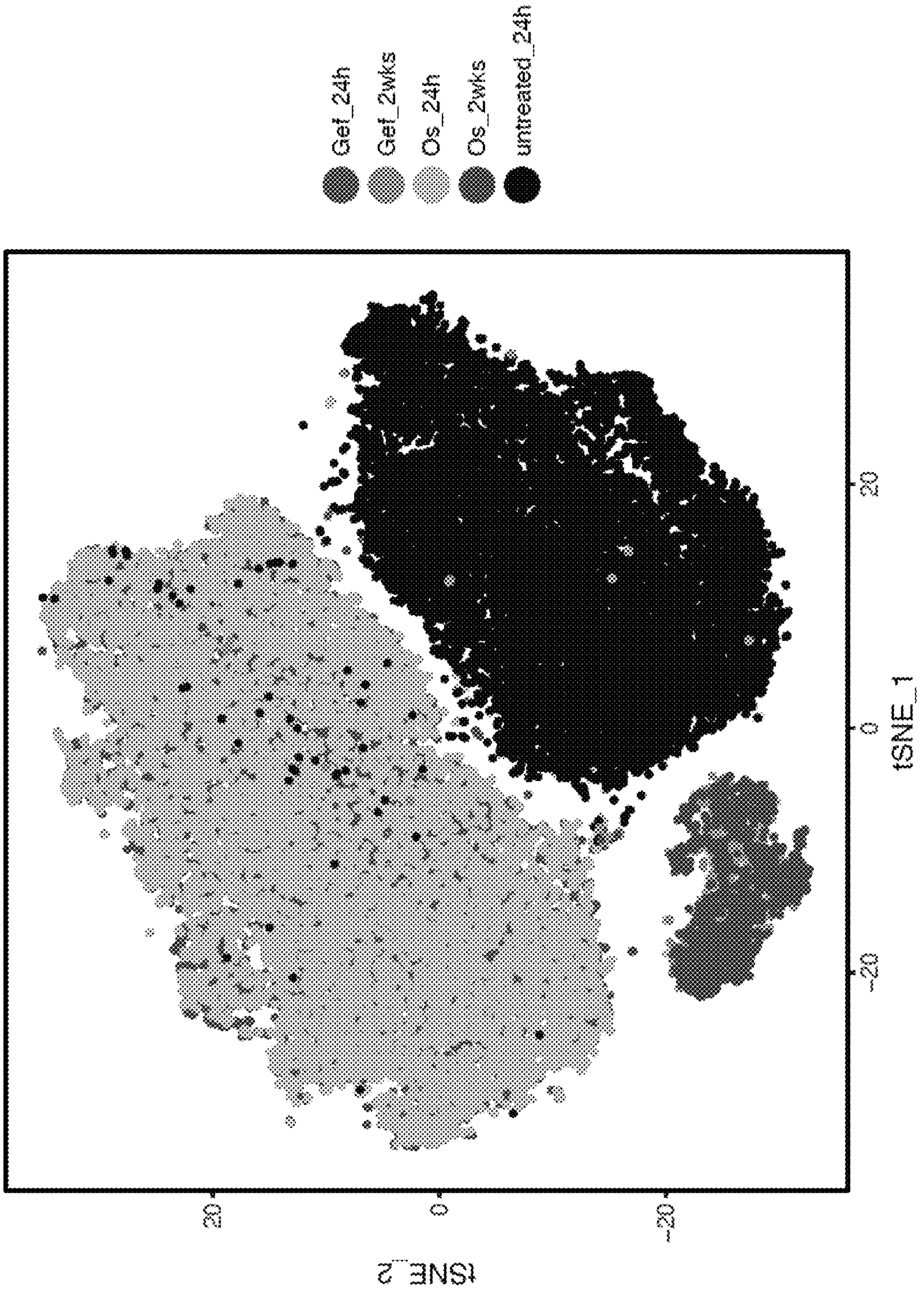

100,000 Watermelon-transduced PC-9 cells were seeded and proliferated to around 2 million cells. On Day 0, 300,000 cells were seeded per well per treatment. The treatments were as follows: 1) No treatment, 2) gefitinib 300 nM, and 3) osimertinib 300 nM. Lineage and transcriptome analyses were carried out 24 h post treatment and 2 weeks post treatment (FIG. 7A). The lineage barcode was detected in ~43% of cells (FIG. 7B) and as expected, the samples clustered by time and not by drug (FIG. 7C).

Figure 8:
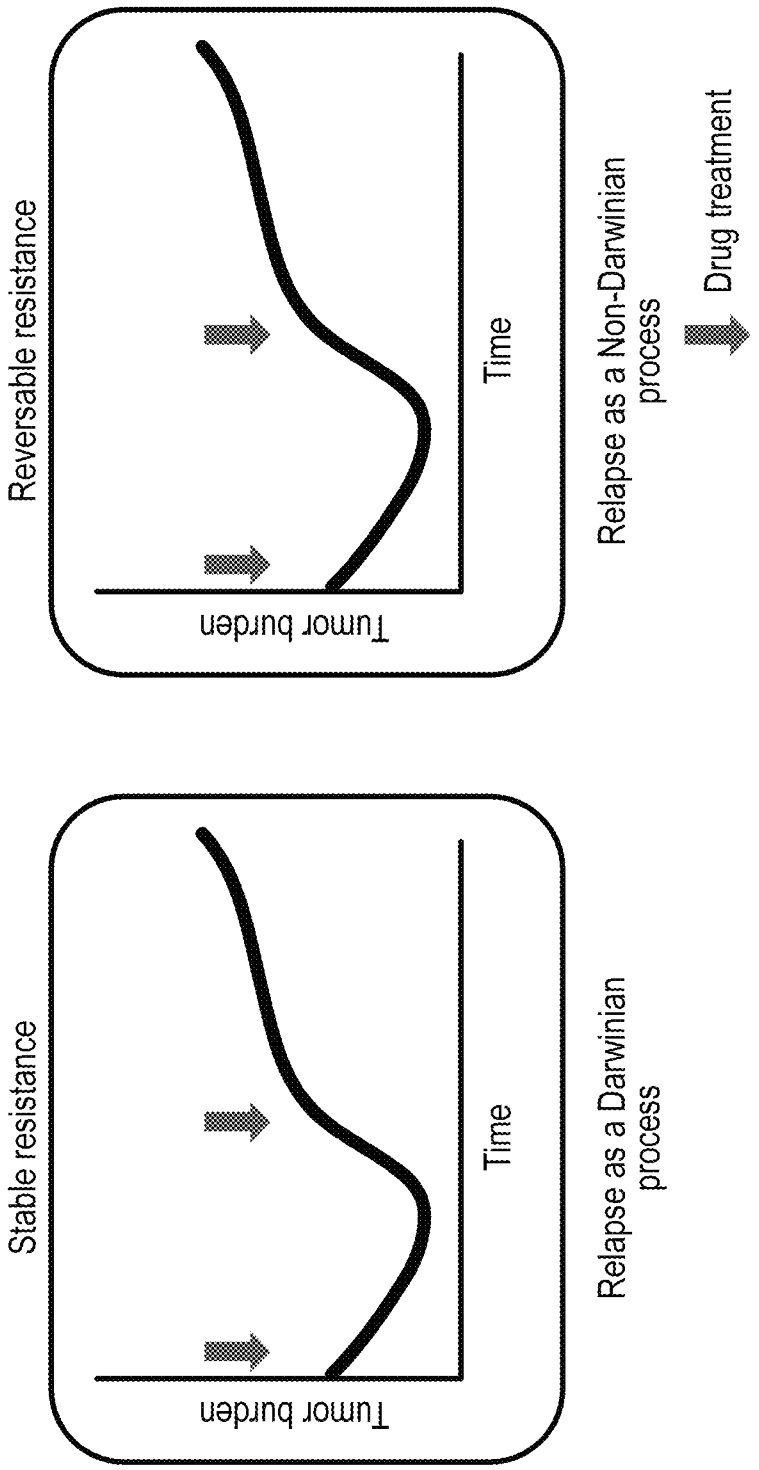
FIG. 8 shows the difference between cancer relapse as a Darwinian or non-Darwinian process.

Example 8. Using Watermelons to Uncover Metabolic Adaptations of Cancer Persister Cells Despite a favorable initial response, many cancer patients will experience recurrence of disease within months to years of diagnosis. The ability of a subset of cells a to survive treatment is frequently attributed to genetic heterogeneity. However, in many types of cancers, the recurrent disease remains sensitive to first-line therapy, suggesting a non-Darwinian process (FIG. 8).

Figure 9A:
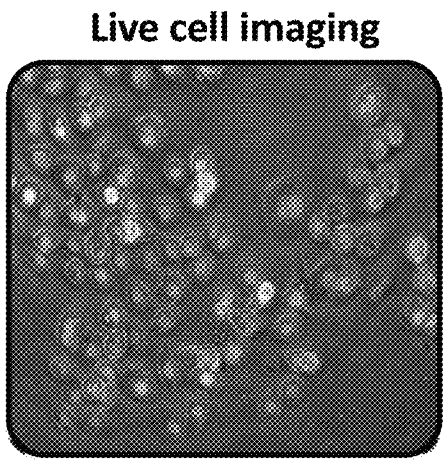
FIGS. 9A-9C shows how the Watermelon library facilitates simultaneously tracing of lineage as well as of transcriptional and proliferative state of each cell in the population. (9A) Shows live cell imaging of watermelon cells expressing two nuclear markers. (9B) Shows proliferation tracking with fluorescence diluted as the cells divide. (9C) Shows lineage tracing of 41,886 Watermelon cells. A single lineage is marked by a distinct identifier. (SEQ ID NO: 1)
Figure 9B:
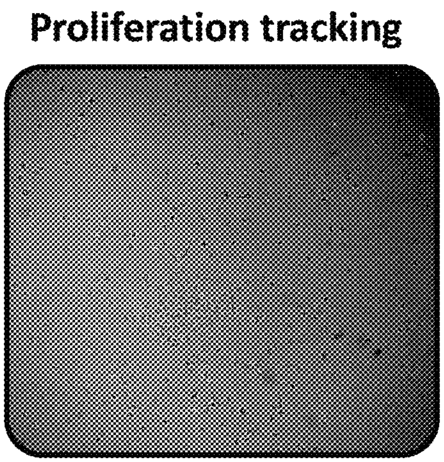
Figure 9C:
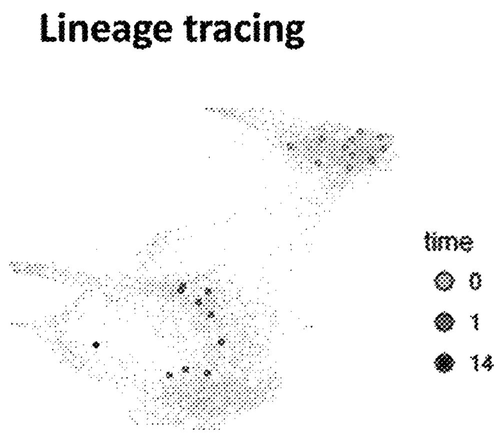
Figure 10:
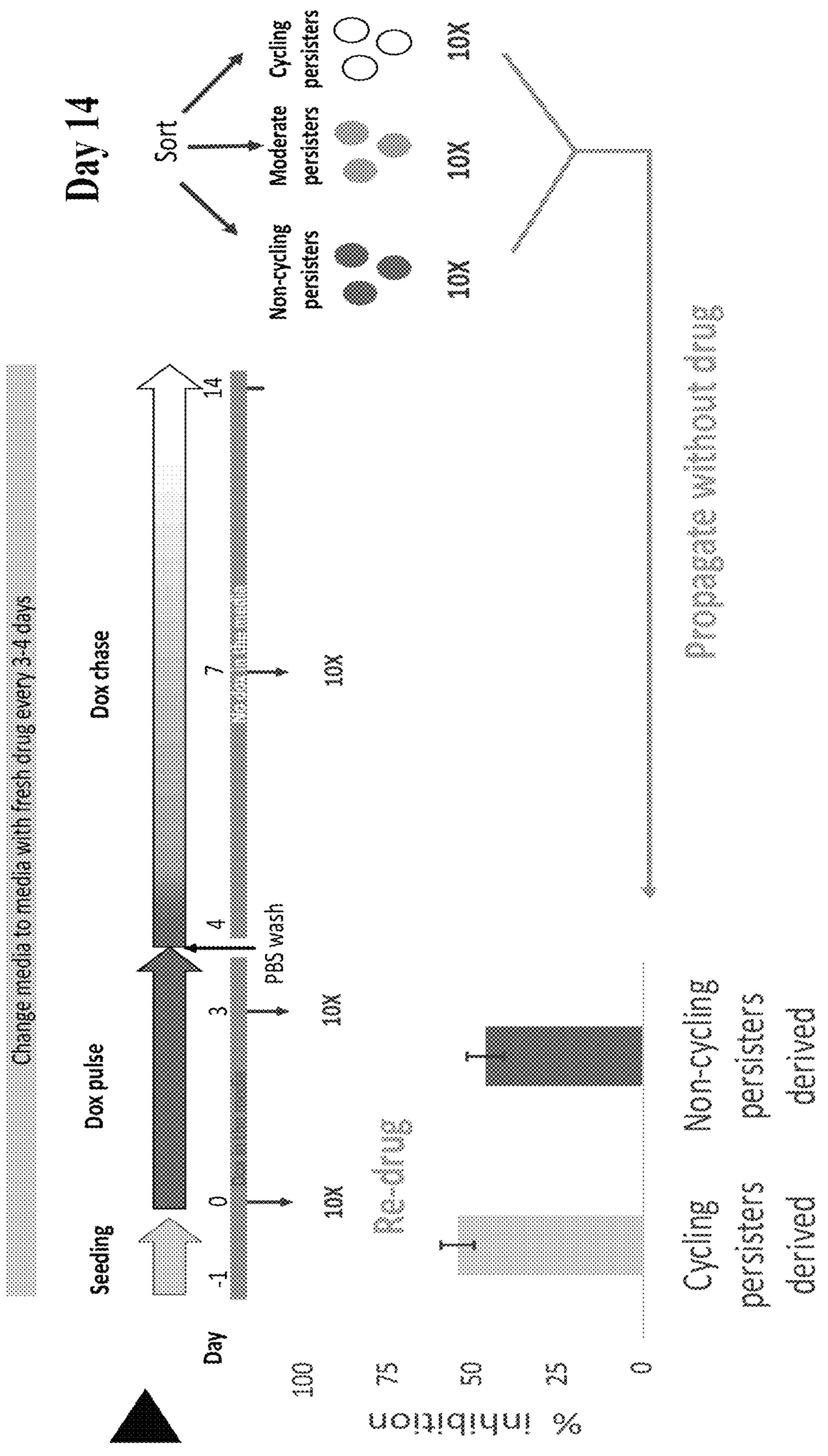
FIG. 10 shows the experimental design used to identify metabolic adaptations of cancer persister cells.
Figure 11:
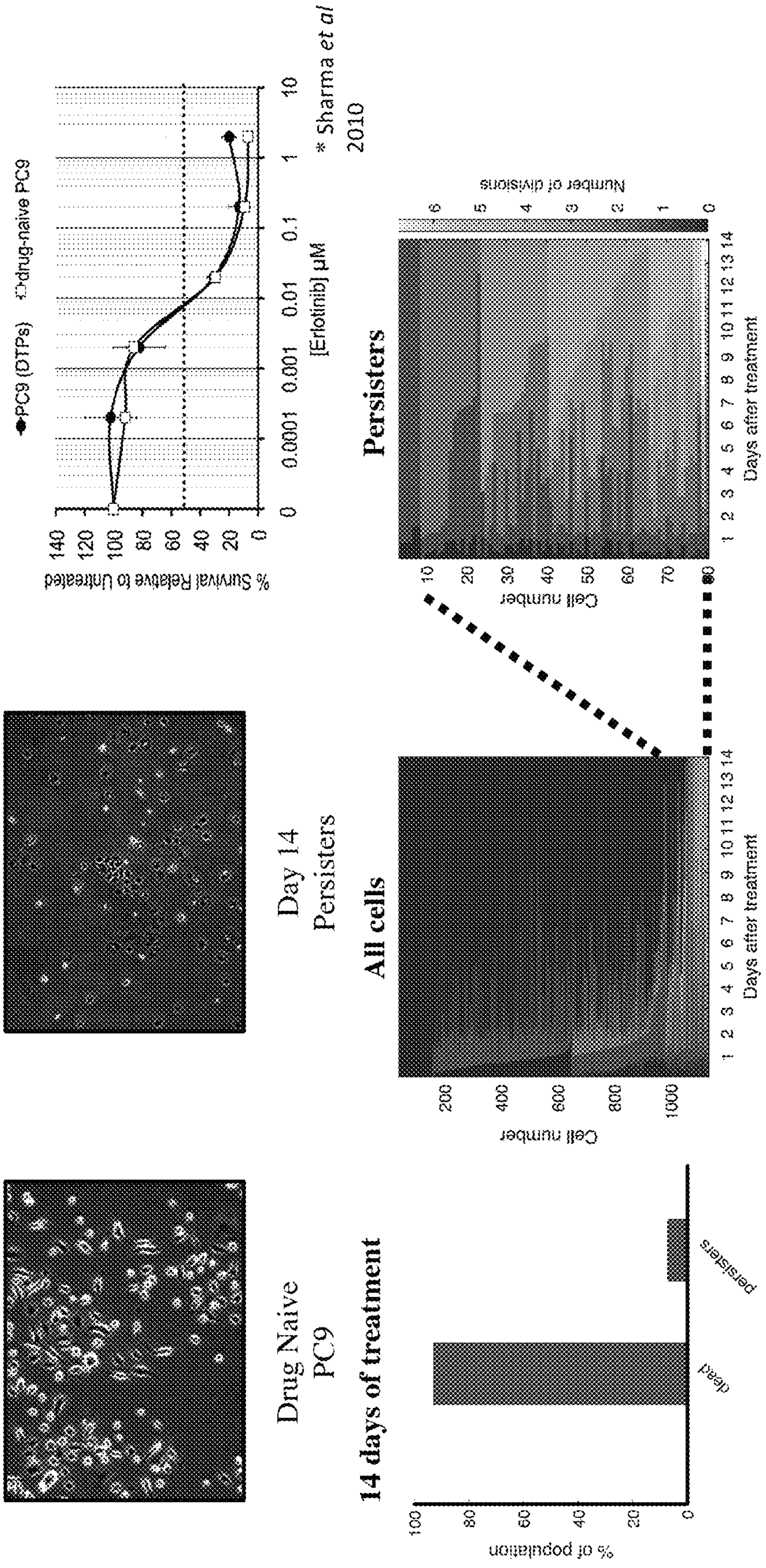
FIG. 11 illustrates the role of cancer persister cells in driving non-Darwinian relapse.

The Watermelon library facilitates simultaneously tracing of lineage as well as of transcriptional and proliferative state of each cell in the population. Cells transduced with the Watermelon vector are shown in FIGS. 3B and 9A. As described in Example 2, the library has three unique features. The first is high throughput live cell imaging. Cells transduced with Watermelon constitutively express both nuclear markers; a green fluorescent reporter (NLS-mNeon) and an additional red reporter (H2B-mCherry) upon exposure to dox. FIG. 9A shows watermelon cells expressing both nuclear markers. The second unique feature of the library is proliferation tracking. As shown in FIG. 9B, the red fluorescence is diluted as the cells divide. The third feature is lineage tracing at the transcriptome level. This feature allows for marking of a single lineage by color, as shown in FIG. 9C.

Persisters are a subpopulation of transiently drug-tolerant cells that are able to survive cytotoxic exposure to therapy through a reversible, non-mutational mechanism. Little is known about the mechanisms underlying drug tolerant persisters (DTPs) and why only a small fraction of surviving persister cells can cycle under constant drug treatment. FIG.

Figure 12:
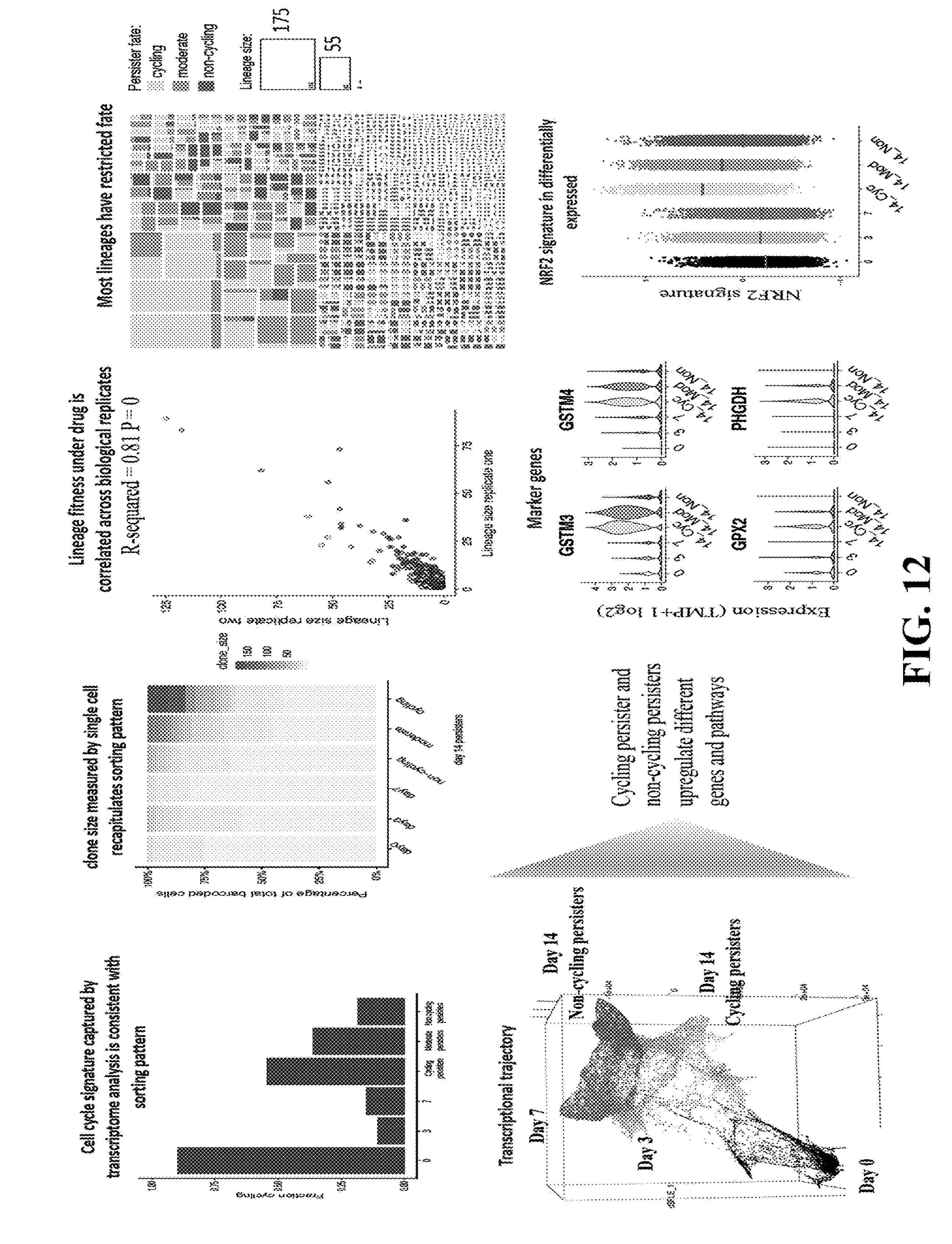
FIG. 12 illustrates how cycling and non-cycling persister cells follow distinct trajectories.
Figure 13A:
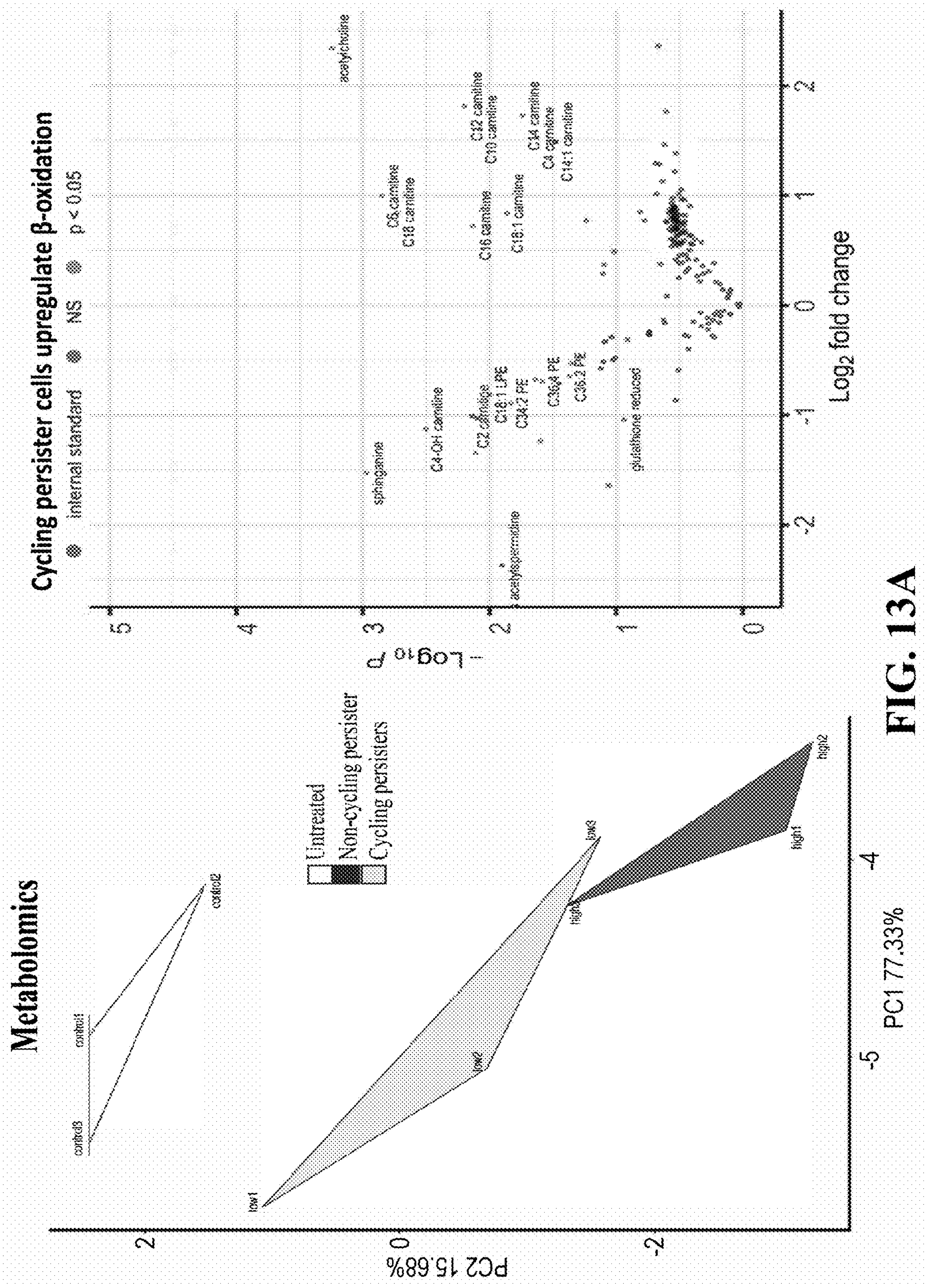
FIGS. 13A-13C illustrate how persister cells switch to fatty acid oxidation.
Figure 13B:
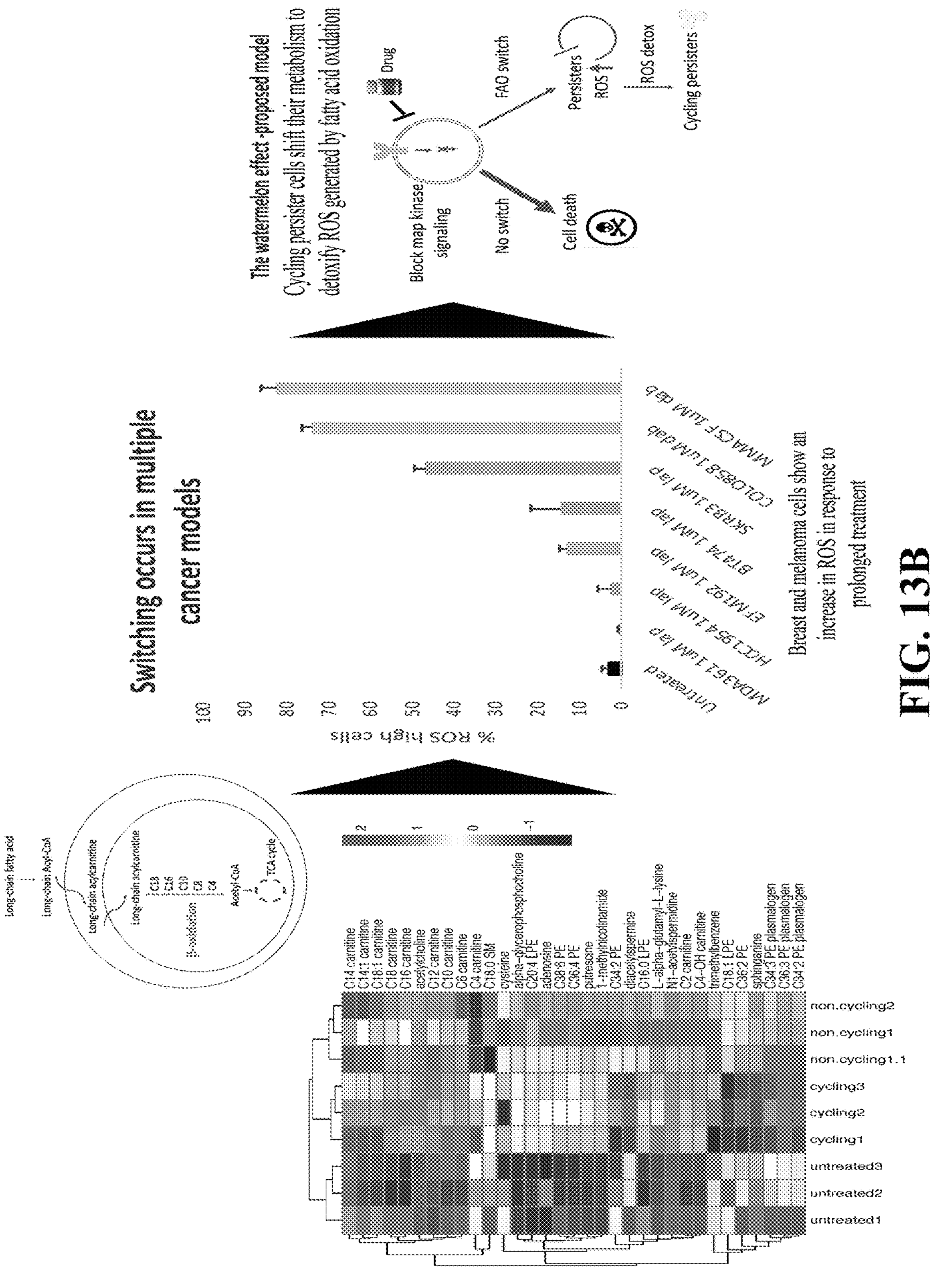
Figure 13C:
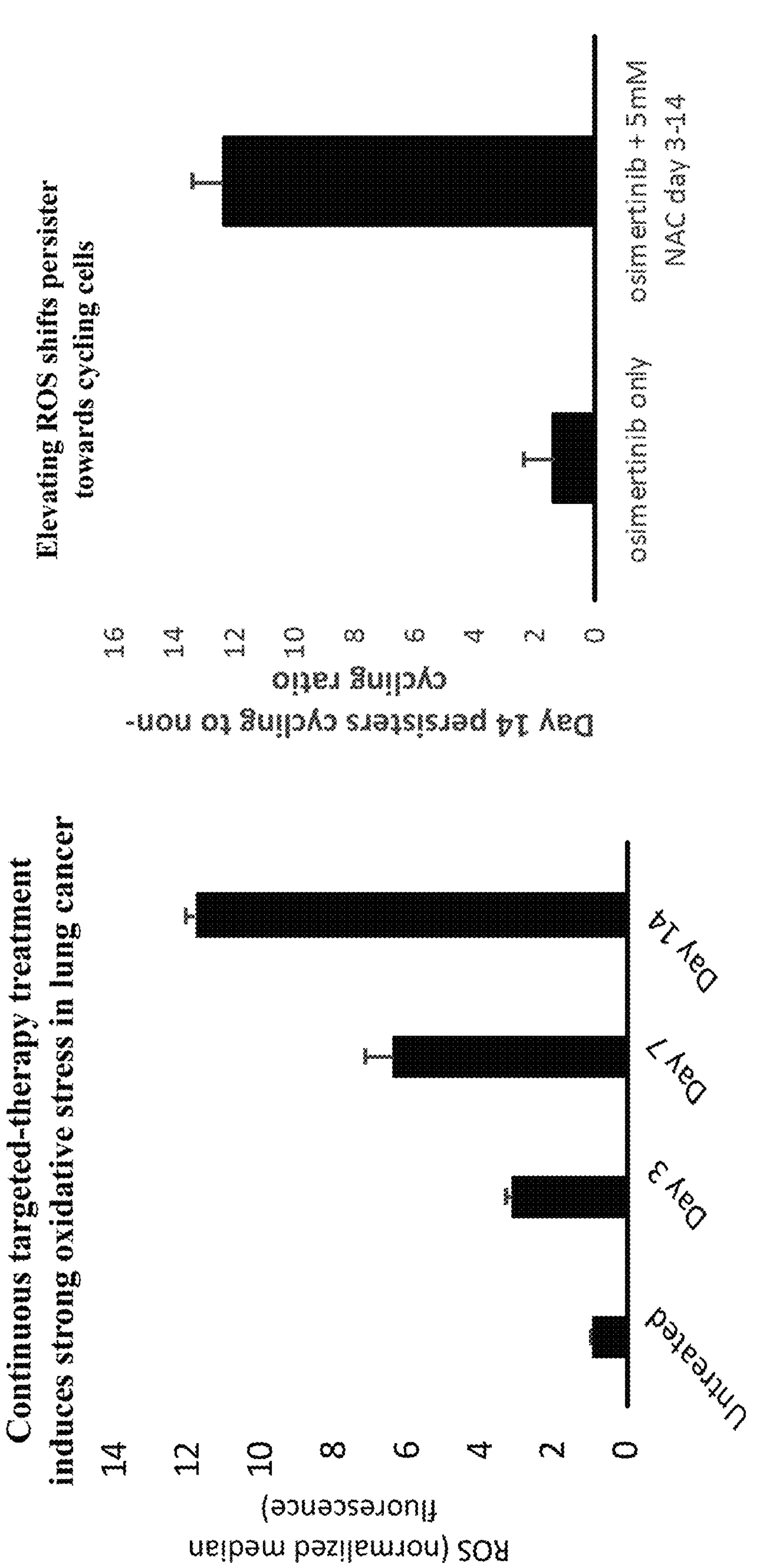

11 shows how many drug tolerant cells persist after 14 days of treatment. FIG. 12 shows how cycling and non-cycling persister cells follow distinct trajectories. In particular, persister cells switch to fatty acid oxidation. FIGS. 13A-13C show that cycling persister cells shift their metabolism to detoxify reactive oxygen species generated by fatty acid oxidation.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

2. The nucleic acid molecule of claim 1, wherein the first reporter gene encodes a fluorescent protein, optionally an mNeon protein, and optionally wherein the first reporter gene further comprises a nuclear localization signal (NLS).

3. The nucleic acid molecule of claim 2, wherein the fluorescent protein is selected from the group consisting of: an mNeon protein, a green fluorescent protein (GFP), a red fluorescent protein (RFP), an mCherry protein, a tdTomato protein, an E2 Crimson protein, a Cerulean protein, and an mBanana protein.

4. The nucleic acid molecule of claim 1, wherein the constitutive promoter operably linked to the first reporter gene is selected from the group consisting of: phosphoglycerate kinase 1 (PGK) promoter, simian virus 40 (SV40) promoter, cytomegalovirus (CMV) promoter, ubiquitin C (UBC) promoter, and elongation factor-1 alpha (EF1A) promoter.

5. The nucleic acid molecule of claim 1, wherein the tandem gene expression element is an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A).

6. The nucleic acid molecule of claim 5, wherein the tandem gene expression element is T2A.

What is claimed is:

1. A double stranded nucleic acid molecule comprising:

(i) a first reporter gene construct comprising:
a constitutive promoter;
a tandem gene expression element; and
a first reporter gene operably linked to the constitutive promoter;

(ii) a second reporter gene construct comprising:
an inducible promoter; and
a second reporter gene operably linked to the inducible promoter; and (iii) a transcribable molecular barcode having a variable sequence and operably linked to the constitutive promoter, wherein the tandem gene expression element is located downstream of the constitutive promoter and upstream of the first reporter gene and the transcribable molecular barcode is located downstream of the first reporter gene, and wherein the first reporter gene construct and the second reporter gene construct are in divergent orientation relative to each other on the double stranded nucleic acid molecule such that the constitutive promoter is not operably linked to the second reporter gene and the inducible promoter is not operably linked to the first reporter gene.

7. The nucleic acid molecule of claim 1, wherein the second reporter gene encodes a fluorescent protein, and wherein the fluorescent protein is selected from the group consisting of: an mNeon protein, a green fluorescent protein (GFP), a red fluorescent protein (RFP), an mCherry protein, a tdTomato protein, an E2 Crimson protein, a Cerulean protein, and an mBanana protein.

8. The nucleic acid molecule of claim 1, wherein the first reporter gene and the second reporter gene encode fluorescent proteins that are distinguishable from each other.

9. The nucleic acid molecule of claim 1, wherein the second reporter gene encodes a histone binding protein fused to a fluorescent protein, wherein the histone binding protein fused to a fluorescent protein is H2B-mCherry.

10. The nucleic acid molecule of claim 1, wherein the inducible promoter operably linked to the second reporter gene is selected from the group consisting of: a light inducible promoter, a chemically inducible promoter, and an energy inducible promoter.

11. The nucleic acid molecule of claim 10, wherein the energy inducible promoter is inducible by using electromagnetic radiation, sound energy, chemical energy, or thermal energy; wherein the light inducible promoter is a phytochrome, a Light-Oxygen-Voltage (LOV) domain, or a cryptochrome; or wherein the chemically inducible promoter is a tetracycline inducible promoter.

12. The nucleic acid molecule of claim 11, wherein the tetracycline inducible promoter is a tetracycline-responsive element (TRE).

13. The nucleic acid molecule of claim 12, wherein the first reporter gene construct further comprises a Tet-on transactivator coding sequence, and wherein the Tet-on transactivator coding sequence is operably linked to the constitutive promoter operably linked to the first reporter gene.

14. The nucleic acid molecule of claim 1, wherein the transcribable molecular barcode comprises a semi-random sequence and has a length of 10-15, 15-20, 20-25, 25-30, or 30-35 nucleotides.

15. The nucleic acid molecule of claim 1, wherein the transcribable molecular barcode further comprises one or more amplification sequences.

16. A vector comprising the nucleic acid molecule according to claim 1.

17. The vector of claim 16, wherein the vector is a plasmid.

18. The vector of claim 16, wherein the vector is a viral vector selected from the group consisting of: herpes simplex virus (HSV) vectors, vaccinia virus vectors, cytomegalovirus vectors, moloney murine leukemia virus vectors, adenovirus vectors, adeno-associated virus vectors, retrovirus vectors, and lentivirus vectors.

19. A cell comprising the nucleic acid molecule of claim 1, optionally wherein the cell is a cancer cell.

20. A cell comprising the vector of claim 16, optionally wherein the cell is a cancer cell.

21. A population of nucleic acid molecules according to claim 1, wherein there are at least 50,000 different transcribable molecular barcode sequences in the population.

22. A vector library comprising the population of nucleic acid molecules of claim 21.

23. The vector library of claim 22, wherein the vectors are plasmids.

24. The vector library of claim 22, wherein the vectors are viral vectors, optionally selected from the group consisting of: herpes simplex virus (HSV) vectors, vaccinia virus vectors, cytomegalovirus vectors, moloney murine leukemia virus vectors, adenovirus vectors, adeno-associated virus vectors, retrovirus vectors, and lentivirus vectors.

25. A population of cells comprising the population of nucleic acid molecules of claim 21.

26. A population of cells comprising the vector library of claim 22.

27. The population of cells of claim 25, wherein the cells are cancer cells derived from cell lines or stable cell cultures.

28. The population of cells of claim 26, wherein the cells are cancer cells derived from cell lines or stable cell cultures.

29. A method of genetically barcoding a cell, a population of cells, or a culture of cells, comprising:

(i) providing a cell, a population of cells or a culture of cells;

(ii) providing at least one nucleic acid molecule according to claim 1, wherein the at least one nucleic acid is contained within a vector capable of stably transfecting, transducing, or infecting the cell, the population of cells, or the culture of cells; and (iii) transfecting, transducing, or infecting the cell, the population of cells, or the culture of cells with the vector, leading to the integration of an individual molecular barcode into the genomic DNA of the cell or each cell of the population or culture of cells, thereby genetically barcoding the cell, the population of cells, or the culture of cells.

30. A method of simultaneously profiling the cell lineage and transcriptional state of single cells in a population of cells comprising:

(i) stably transfecting, transducing, or infecting a population of cells with a vector library according to claim 22;

(ii) allowing for transcription of the molecular barcode, the first reporter gene, and the second reporter gene;

(iii) profiling the transcriptome of single cells in the population of cells by single cell sequencing; and (iv) associating the lineage of a single cell within the population with its transcriptional profile based on the expression of the molecular barcode.

31. A method of identifying genes associated with tumor dormancy comprising:

(i) stably transfecting, transducing, or infecting a population of cells with a vector library according to claim 22, wherein the detection of the gene product of the second reporter gene is indicative of the proliferative status of the cell, (ii) propagating and dividing the cells into identical control and treatment replicate groups;

(iii) profiling the transcriptome and lineage of single cells in the control replicate group;

(iv) treating the treatment replicate group with a cancer therapeutic;

(v) profiling the transcriptome and lineage of single cells in the treatment replicate group in the lag phase following the treatment;

(vi) profiling the transcriptome and lineage of single cells in the treatment replicate group following relapse;

(vii) deriving gene signatures from (iii), (v) and (vi); and (viii) comparing the gene signatures derived from (iii), (v) and (vi) to identify genes associated with tumor dormancy.

32. The method of claim 31, further comprising measuring the dilution of gene product of the second reporter over time, wherein the dilution is indicative of proliferative history.

33. A method of identifying genes associated with stem-cell like treatment-resistant cancer cells comprising:

(i) stably transfecting, transducing, or infecting a population of cells with a vector library according to claim 22;

(ii) propagating and dividing the cells into identical control and treatment replicate groups;

(iii) profiling the transcriptome and lineage of single cells in the control replicate group;

(iv) treating the treatment replicate group with a cancer therapeutic;

(v) profiling the transcriptome and lineage of single cells in the treatment replicate group in the lag phase following the treatment;

(vi) profiling the transcriptome and lineage of single cells in the treatment replicate group following relapse;

(vii) deriving gene signatures from (iii), (v) and (vi); and (viii) comparing the gene signatures derived from (iii), (v) and (vi) to identify genes associated with stem-cell like treatment-resistant cancer cells.

34. The population of cells of claim 25, wherein the population of cells comprises a subpopulation of cells positive for the gene product of the second reporter gene, and wherein the detection of the gene product of the second reporter gene is indicative of the proliferative status of a cell of the population.

35. The population of cells of claim 25, wherein individual cells of the population of cells each contain a gene product of the second reporter gene in a concentration that is indicative of the proliferative status of each of the individual cells.

36. A population of cells, each of the population of cells comprising at least one of the population of nucleic acid molecules of claim 21.

37. The population of cells of claim 36, wherein individual cells of the population of cells each contain a gene product of the second reporter gene in a concentration that is indicative of the proliferative status of each of the individual cells.

* * * * *

SEQUENCE LISTING

```
<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1

tctgtcagtg tcacagtcac tctcactgtc                                        30
```